(12) United States Patent
Schacht et al.

(10) Patent No.: US 11,241,658 B2
(45) Date of Patent: Feb. 8, 2022

(54) COMPOSITIONS AND METHODS FOR THE REDUCTION OF BIOFILM AND SPORES FROM MEMBRANES

(71) Applicant: Ecolab USA Inc., St. Paul, MN (US)

(72) Inventors: Paul Frazer Schacht, Oakdale, MN (US); Nikolaus Nathan Schultz, Plymouth, MN (US); Caleb Myunghoon Ford Power, St. Paul, MN (US); Cynthia Ann Bunders, Minneapolis, MN (US); Anthony Wayne Erickson, Golden Valley, MN (US)

(73) Assignee: ECOLAB USA INC., St. Paul, MN (US)

( * ) Notice: Subject to any disclaimer, the term of this patent is extended or adjusted under 35 U.S.C. 154(b) by 0 days.

(21) Appl. No.: 16/274,487

(22) Filed: Feb. 13, 2019

(65) Prior Publication Data
US 2019/0275468 A1    Sep. 12, 2019

Related U.S. Application Data

(60) Provisional application No. 62/630,329, filed on Feb. 14, 2018.

(51) Int. Cl.
*B01D 65/08*   (2006.01)
*C11D 7/26*    (2006.01)
(Continued)

(52) U.S. Cl.
CPC .............. *B01D 65/08* (2013.01); *A61L 2/186* (2013.01); *B01D 65/02* (2013.01); *B01D 65/022* (2013.01);
(Continued)

(58) Field of Classification Search
None
See application file for complete search history.

(56) References Cited

U.S. PATENT DOCUMENTS

| | | |
|---|---|---|
| 2,512,640 A | 6/1950 | Greenspan et al. |
| 3,122,417 A | 2/1964 | Blaser et al. |
| (Continued) | | |

FOREIGN PATENT DOCUMENTS

| | | |
|---|---|---|
| CA | 2181416 | 1/1997 |
| DE | 30 03 875 A1 | 8/1981 |
| (Continued) | | |

OTHER PUBLICATIONS

International Search Report and Written Opinion for Application No. PCT/US2019/017841 dated Apr. 16, 2019.

*Primary Examiner* — Clare M Perrin
(74) *Attorney, Agent, or Firm* — Merchant & Gould P.C.

(57) ABSTRACT

Methods of cleaning and sanitizing membrane modules within a membrane system are provided. A cleaning solution is circulated through the membrane system for about 2 to about 30 minutes. The cleaning solution includes organic acid and surfactant. A sanitizing solution is added to the cleaning solution to produce a boosted antimicrobial solution comprising an oxidizer. The boosted antimicrobial solution is then circulated through the membrane system for about 1 to about 20 minutes. The methods described are effective for reducing and removing bacterial spores and biofilms from membranes and improving membrane compatibility of effective cleaning and sanitizing solutions.

16 Claims, 16 Drawing Sheets

(51) Int. Cl.

| | | |
|---|---|---|
| *C11D 3/20* | (2006.01) | |
| *C11D 3/48* | (2006.01) | |
| *B01D 65/02* | (2006.01) | |
| *A61L 2/18* | (2006.01) | |
| *C11D 3/04* | (2006.01) | |
| *C11D 11/00* | (2006.01) | |
| *B01D 71/02* | (2006.01) | |
| *B01D 71/06* | (2006.01) | |
| *C02F 1/44* | (2006.01) | |
| *C02F 5/10* | (2006.01) | |
| *C02F 1/72* | (2006.01) | |
| *B01D 61/02* | (2006.01) | |
| *B01D 63/02* | (2006.01) | |
| *B01D 63/06* | (2006.01) | |
| *B01D 63/08* | (2006.01) | |
| *B01D 63/10* | (2006.01) | |
| *B01D 61/14* | (2006.01) | |

(52) U.S. Cl.
CPC ........... *B01D 71/022* (2013.01); *B01D 71/06* (2013.01); *C11D 3/042* (2013.01); *C11D 3/20* (2013.01); *C11D 3/48* (2013.01); *C11D 7/265* (2013.01); *C11D 11/0023* (2013.01); *A61L 2202/17* (2013.01); *B01D 61/02* (2013.01); *B01D 61/145* (2013.01); *B01D 63/02* (2013.01); *B01D 63/06* (2013.01); *B01D 63/08* (2013.01); *B01D 63/10* (2013.01); *B01D 2321/162* (2013.01); *B01D 2321/168* (2013.01); *B01D 2321/28* (2013.01); *B01D 2321/32* (2013.01); *C02F 1/44* (2013.01); *C02F 1/722* (2013.01); *C02F 5/10* (2013.01); *C02F 2303/16* (2013.01); *C02F 2303/20* (2013.01); *C02F 2305/04* (2013.01)

(56) References Cited

U.S. PATENT DOCUMENTS

| | | |
|---|---|---|
| 3,248,281 A | 4/1966 | Goodenough |
| 3,350,265 A | 10/1967 | Rubinstein et al. |
| 3,514,278 A | 5/1970 | Brink |
| 3,895,116 A | 7/1975 | Herting et al. |
| 3,996,386 A | 12/1976 | Malkki et al. |
| 4,041,149 A | 8/1977 | Gaffar et al. |
| 4,051,058 A | 9/1977 | Böwing et al. |
| 4,051,059 A | 9/1977 | Böwing et al. |
| 4,129,517 A | 12/1978 | Eggensperger et al. |
| 4,191,660 A | 3/1980 | Schreiber et al. |
| 4,244,884 A | 1/1981 | Hutchins et al. |
| 4,289,728 A | 9/1981 | Peel et al. |
| 4,321,157 A | 3/1982 | Harris et al. |
| 4,370,199 A | 1/1983 | Orndorff |
| 4,404,040 A | 9/1983 | Wang |
| 4,477,438 A | 10/1984 | Willcockson et al. |
| 4,478,683 A | 10/1984 | Orndorff |
| 4,501,681 A | 2/1985 | Groult et al. |
| 4,529,534 A | 7/1985 | Richardson |
| 4,557,898 A | 12/1985 | Greene et al. |
| 4,566,980 A | 1/1986 | Smith |
| 4,591,565 A | 5/1986 | Branner-Jorgensen |
| 4,592,488 A | 6/1986 | Simon et al. |
| 4,613,452 A | 9/1986 | Sanderson |
| 4,655,781 A | 4/1987 | Hsieh et al. |
| 4,659,494 A | 4/1987 | Soldanski et al. |
| 4,666,622 A | 5/1987 | Martin et al. |
| 4,683,618 A | 8/1987 | O'Brien |
| 4,704,404 A | 11/1987 | Sanderson |
| 4,715,980 A | 12/1987 | Lopes et al. |
| 4,738,840 A | 4/1988 | Simon et al. |
| 4,802,994 A | 2/1989 | Mouche et al. |
| 4,834,900 A | 5/1989 | Soldanski et al. |
| 4,865,752 A | 9/1989 | Jacobs |
| 4,900,721 A | 2/1990 | Bansemir et al. |
| 4,906,617 A | 3/1990 | Jacquet et al. |
| 4,908,306 A | 3/1990 | Lorincz |
| 4,917,815 A | 4/1990 | Beilfuss et al. |
| 4,923,677 A | 5/1990 | Simon et al. |
| 4,937,066 A | 6/1990 | Vlock |
| 4,943,414 A | 7/1990 | Jacobs et al. |
| 4,945,110 A | 7/1990 | Brokken et al. |
| 4,996,062 A | 2/1991 | Lehtonen et al. |
| 4,997,571 A | 3/1991 | Roensch et al. |
| 4,997,625 A | 3/1991 | Simon et al. |
| 5,004,760 A | 4/1991 | Patton et al. |
| 5,010,109 A | 4/1991 | Inoi |
| 5,015,408 A | 5/1991 | Reuss |
| 5,043,176 A | 8/1991 | Bycroft et al. |
| 5,069,286 A | 12/1991 | Roensch et al. |
| 5,078,896 A | 1/1992 | Rorig et al. |
| 5,084,239 A | 1/1992 | Moulton et al. |
| 5,093,140 A | 3/1992 | Watanabe |
| 5,114,178 A | 5/1992 | Baxter |
| 5,114,718 A | 5/1992 | Damani |
| 5,122,538 A | 6/1992 | Lokkesmoe et al. |
| 5,129,824 A | 7/1992 | Keller |
| 5,130,124 A | 7/1992 | Merianos et al. |
| 5,139,788 A | 8/1992 | Schmidt |
| 5,168,655 A | 12/1992 | Davidson et al. |
| 5,176,899 A | 1/1993 | Montgomery |
| 5,184,471 A | 2/1993 | Losacco et al. |
| 5,200,189 A | 4/1993 | Oakes et al. |
| 5,208,057 A | 5/1993 | Greenley et al. |
| 5,234,703 A | 8/1993 | Guthery |
| 5,234,719 A | 8/1993 | Richter et al. |
| 5,266,587 A | 11/1993 | Sankey et al. |
| 5,268,003 A | 12/1993 | Coope et al. |
| 5,292,447 A | 3/1994 | Venturello et al. |
| 5,314,687 A | 5/1994 | Oakes et al. |
| 5,320,805 A | 6/1994 | Kramer et al. |
| 5,336,500 A | 8/1994 | Richter et al. |
| 5,364,650 A | 11/1994 | Guthery |
| 5,391,324 A | 2/1995 | Reinhardt et al. |
| 5,409,713 A | 4/1995 | Lokkesmoe et al. |
| 5,419,908 A | 5/1995 | Richter et al. |
| 5,435,808 A | 7/1995 | Holzhauer et al. |
| 5,436,008 A | 7/1995 | Richter et al. |
| 5,437,868 A | 8/1995 | Oakes et al. |
| 5,489,434 A | 2/1996 | Oakes et al. |
| 5,489,706 A | 2/1996 | Revell |
| 5,494,588 A | 2/1996 | LaZonby |
| 5,508,046 A | 4/1996 | Cosentino et al. |
| 5,512,309 A | 4/1996 | Bender et al. |
| 5,527,898 A | 6/1996 | Bauer et al. |
| 5,545,343 A | 8/1996 | Brougham et al. |
| 5,545,374 A | 8/1996 | French et al. |
| 5,578,134 A | 11/1996 | Lentsch et al. |
| 5,591,706 A | 1/1997 | Ploumen |
| 5,595,967 A | 1/1997 | Miracle et al. |
| 5,597,790 A | 1/1997 | Thoen |
| 5,616,335 A | 4/1997 | Nicolle et al. |
| 5,616,616 A | 4/1997 | Hall et al. |
| 5,624,634 A | 4/1997 | Brougham et al. |
| 5,632,676 A | 5/1997 | Kurschner et al. |
| 5,641,530 A | 6/1997 | Chen |
| 5,656,302 A | 8/1997 | Cosentino et al. |
| 5,658,467 A | 8/1997 | LaZonby et al. |
| 5,658,595 A | 8/1997 | Van Os |
| 5,670,055 A | 9/1997 | Yu et al. |
| 5,674,538 A | 10/1997 | Lokkesmoe et al. |
| 5,674,828 A | 10/1997 | Knowlton et al. |
| 5,683,724 A | 11/1997 | Hei et al. |
| 5,712,239 A | 1/1998 | Knowlton et al. |
| 5,718,910 A | 2/1998 | Oakes et al. |
| 5,720,983 A | 2/1998 | Malone |
| 5,756,139 A | 5/1998 | Harvey et al. |
| 5,785,867 A | 7/1998 | LaZonby et al. |
| 5,840,343 A | 11/1998 | Hall et al. |
| 5,851,483 A | 12/1998 | Nicolle et al. |
| 5,891,392 A | 4/1999 | Monticello et al. |
| 5,900,256 A | 5/1999 | Scoville, Jr. et al. |
| 5,902,619 A | 5/1999 | Rubow et al. |

(56) References Cited

U.S. PATENT DOCUMENTS

| | | |
|---|---|---|
| 5,962,392 A | 10/1999 | Revell et al. |
| 5,968,539 A | 10/1999 | Beerse et al. |
| 5,989,611 A | 11/1999 | Stemmler, Jr. et al. |
| 5,998,358 A | 12/1999 | Herdt et al. |
| 6,008,405 A | 12/1999 | Gray et al. |
| 6,010,729 A | 1/2000 | Gutzmann et al. |
| 6,024,986 A | 2/2000 | Hei |
| 6,028,104 A | 2/2000 | Schmidt et al. |
| 6,033,705 A | 3/2000 | Isaacs |
| 6,039,992 A | 3/2000 | Compardre et al. |
| 6,049,002 A | 4/2000 | Mattila et al. |
| 6,080,712 A | 6/2000 | Revell et al. |
| 6,096,226 A | 8/2000 | Fuchs et al. |
| 6,096,348 A | 8/2000 | Miner et al. |
| 6,103,286 A | 8/2000 | Gutzmann et al. |
| 6,113,963 A | 9/2000 | Gutzmann et al. |
| 6,165,483 A | 12/2000 | Hei et al. |
| 6,183,807 B1 | 2/2001 | Gutzmann et al. |
| 6,238,685 B1 | 5/2001 | Hei et al. |
| 6,257,253 B1 | 7/2001 | Lentsch et al. |
| 6,274,542 B1 | 8/2001 | Carr et al. |
| 6,302,968 B1 | 10/2001 | Baum et al. |
| 6,395,703 B2 | 5/2002 | Scepanski |
| 6,423,868 B1 | 7/2002 | Carr et al. |
| 6,451,746 B1 | 9/2002 | Moore et al. |
| 6,489,281 B1 | 12/2002 | Smith et al. |
| 6,514,556 B2 | 2/2003 | Hilgren et al. |
| 6,545,047 B2 | 4/2003 | Gutzmann et al. |
| 6,627,657 B1 | 9/2003 | Hilgren et al. |
| 6,630,439 B1 | 10/2003 | Norwood et al. |
| 6,635,286 B2 | 10/2003 | Hei et al. |
| 6,638,902 B2 | 10/2003 | Tarara et al. |
| 6,927,237 B2 | 8/2005 | Hei et al. |
| 6,964,787 B2 | 11/2005 | Swart et al. |
| 7,049,277 B2 | 5/2006 | Bragulla et al. |
| 7,150,884 B1 | 12/2006 | Hilgren et al. |
| 7,220,358 B2 | 5/2007 | Schacht et al. |
| 7,569,232 B2 | 8/2009 | Man et al. |
| 7,771,737 B2 | 8/2010 | Man et al. |
| 7,832,360 B2 | 11/2010 | Hilgren et al. |
| 8,057,812 B2 | 11/2010 | Man et al. |
| 8,062,381 B2 | 11/2011 | Shamayeli et al. |
| 8,278,259 B2 | 10/2012 | Shamayeli et al. |
| 8,318,188 B2 | 11/2012 | Man et al. |
| 8,758,789 B2 | 6/2014 | Man et al. |
| 9,072,315 B2 | 7/2015 | Nolen et al. |
| 2002/0128312 A1 | 9/2002 | Hei et al. |
| 2002/0168422 A1 | 11/2002 | Hei et al. |
| 2003/0015219 A1 | 1/2003 | Kravitz et al. |
| 2003/0070691 A1 | 4/2003 | Giletto et al. |
| 2003/0087786 A1 | 5/2003 | Hei et al. |
| 2003/0199583 A1 | 10/2003 | Gutzmann et al. |
| 2004/0140259 A1 | 7/2004 | Cummings |
| 2005/0126599 A1 | 6/2005 | Labib et al. |
| 2006/0089281 A1 | 4/2006 | Gibson |
| 2008/0031970 A1 | 2/2008 | Benedict et al. |
| 2008/0169006 A1 | 7/2008 | Musale et al. |
| 2008/0221006 A1 | 9/2008 | Heisig et al. |
| 2008/0264454 A1 | 10/2008 | Tabani et al. |
| 2009/0200234 A1* | 8/2009 | Schacht ................ C11D 3/08 210/636 |
| 2010/0000579 A1 | 1/2010 | Reinbold et al. |
| 2011/0259367 A1 | 10/2011 | Ahmed et al. |
| 2011/0312865 A1 | 12/2011 | Hodge et al. |
| 2012/0289448 A1 | 11/2012 | Man et al. |
| 2014/0309403 A1 | 10/2014 | Brown et al. |
| 2017/0173642 A1* | 6/2017 | Li ..................... C11D 11/0023 |

FOREIGN PATENT DOCUMENTS

| | | |
|---|---|---|
| DE | 35 43 500 A1 | 6/1987 |
| DE | 39 06 044 A1 | 8/1990 |
| EP | 0 125 781 | 11/1984 |
| EP | 0 140 648 | 5/1985 |
| EP | 0 186 052 | 7/1986 |
| EP | 186052 | 7/1986 |
| EP | 0 195 619 A2 | 9/1986 |
| EP | 0 233 731 A2 | 8/1987 |
| EP | 0 233 731 | 9/1987 |
| EP | 0 242 990 A2 | 10/1987 |
| EP | 0 361 955 A2 | 4/1990 |
| EP | 0 404 293 A2 | 12/1990 |
| EP | 0 460 962 | 12/1991 |
| EP | 0 461 700 A1 | 12/1991 |
| EP | 0 569 066 A1 | 11/1993 |
| EP | 0 667 392 A2 | 2/1995 |
| EP | 0 779 357 A1 | 12/1995 |
| EP | 0 805 198 A1 | 7/1996 |
| EP | 0 843 001 A1 | 11/1996 |
| EP | 0 881 883 B1 | 7/2002 |
| EP | 1 382 666 A1 | 1/2004 |
| EP | 2 338 343 A1 | 6/2011 |
| FR | 2 324 626 A | 4/1977 |
| FR | 2 578 988 | 9/1986 |
| GB | 1577396 | 10/1980 |
| GB | 2 182 051 | 5/1987 |
| GB | 2 187 958 | 9/1987 |
| GB | 2 207 354 | 2/1989 |
| GB | 2 255 507 | 11/1992 |
| GB | 2 257 630 | 1/1993 |
| GB | 2 353 800 | 3/2001 |
| NL | 9201631 | 9/1992 |
| RU | 2101447 C1 | 8/1996 |
| WO | WO 93/01716 | 2/1993 |
| WO | WO 94/06294 | 3/1994 |
| WO | WO 94/14321 | 7/1994 |
| WO | WO 94/15465 | 7/1994 |
| WO | WO 94/21122 | 9/1994 |
| WO | WO 94/23575 | 10/1994 |
| WO | WO 95/34537 | 12/1995 |
| WO | WO 96/30474 | 10/1996 |
| WO | WO 98/28267 | 7/1998 |
| WO | WO 00/17303 | 3/2000 |
| WO | WO 00/18870 | 4/2000 |

* cited by examiner

FIG. 1

UF membranes 1 & 2

RO membranes 1 & 2

UF membranes 3 & 4

RO membranes 3 & 4

UF membranes 5 & 6

RO membranes 5 & 6

UF membranes 7 & 8

RO membranes 7 & 8

Membrane 9
RO|UF

Membrane 10
RO|UF

Membrane 11
RO|UF

Membrane 12
RO|UF

COMPOSITIONS AND METHODS FOR THE REDUCTION OF BIOFILM AND SPORES FROM MEMBRANES

CROSS-REFERENCE TO RELATED APPLICATION

This application claims the benefit of U.S. Provisional Application No. 62/630,329, filed Feb. 14, 2018, which is hereby incorporated in its entirety.

TECHNICAL FIELD

The present disclosure relates generally to biocidal compositions and methods for reducing and removing and reducing bacterial spores and biofilms. More particularly, the present disclosure relates to biocidal compositions and methods for treating membranes.

BACKGROUND

Membranes

Membranes are used in separation processes or systems to filter or fractionate components in liquids. Various technologies utilize membranes, including those membranes used in the food and beverage industries.

The membranes that can be treated according to the invention include those membranes that are designed for periodic cleaning, and are often utilized in various applications requiring separation by filtration. Exemplary industries that utilize membranes that can be treated according to the invention include the food industry, the beverage industry, the biotechnology industry, the pharmaceutical industry, the chemical industry, and the water purification industry. In the case of the food and beverage industries, products including water, milk, whey, fruit juice, beer, and wine are often processed through a membrane for separation. The water purification industry often relies upon membranes for desalination, contaminant removal, and waste water treatment.

Membranes that can be treated according to the invention include those provided in the form of spiral wound membranes, plate and frame membranes, tubular membranes, capillary membranes, hollow fiber membranes, ceramic membranes, and the like. The membranes can be generally characterized according to the size of the particles being filtered. Four common types of membrane types include microfiltration (MF) membranes, ultrafiltration (UF) membranes, nanofiltration (NF) membranes, and reverse osmosis (RO) membranes. Microfiltration membranes tend to block very fine heterogeneous particles and have pore sizes within the range of about 0.05 µm to about 10 µm. Microfiltration membranes can separate the largest macro molecules of proteins, separation of viruses, bacteria, and other microorganisms in the manufacture of artificial proteins, filtration of beer or wine, separation of various suspended substances, and removal of various kinds of turbidity. Ultrafiltration membranes have pore sizes within the range of about 0.02 µm to 0.1 µm and provide for separation of macro molecular substances with relative molecular mass within the range of about 1 kDa to about 1,000 kDa. An approximate theoretical size of a pore in nanofiltration membranes is about 0.02 µm or less for separation of polyvalent ions. In reverse osmosis, the pore size is theoretically about 0.002 µm or less and can remove a vast majority of monovalent ion substances from water. Because of the pore sizes, each membrane process operates at an optimal pressure. Microfiltration membrane systems generally operate at pressures less than about 30 psig. Ultrafiltration membrane systems generally operate at pressures of about 15-150 psig. Nanofiltration membrane systems generally operate at pressures of about 75-500 psig. Reverse osmosis membrane systems generally operate at pressures of about 200-2000 psig. Membranes can be formed from a variety of materials that are commonly used to form membranes including cellulose acetate, polyamide, polysulfone, vinylidene fluoride, acrylonitrile, stainless steel, ceramic, etc. These various membrane chemical types and other materials of construction may have specific pH, oxidant, solvent, chemical compatibility restrictions, and/or pressure limitations.

A disadvantage in the use of membranes is that during operation, the membranes gradually become fouled. In particular, biofilm growth, spores, organic deposits, and mineral deposits on membranes, including reverse osmosis membranes, nanofiltration membranes, ultrafiltration membranes, and microfiltration membranes, can have detrimental results. Such biofilm growth, spores, organic deposits, and mineral deposits can cause severe flux declines, increased pressure, reduced production, can negatively impact the quality of finished goods, and often result in premature replacement of such membranes.

Bacterial Spores and Biofouling

Endospores are dormant, tough, non-reproductive structures produced by particular species of bacteria in the *Firmicute* phylum. Endospores, or spores, are produced when bacterial cells in their vegetative state are exposed to stress or lack of nutrients. Endospores have a very low metabolic rate and therefore cannot be detected by methods typically employed to rapidly detect vegetative bacterial cells. Further, spores are extremely difficult to kill because they are designed to survive harsh conditions such as UV, heat, disinfectants, desiccation, and starvation. Upon exposure to favorable conditions and nutrients, the spores germinate to produce vegetative cells.

Spore-producing bacteria are problematic because they cause illness in humans and animals, spoilage in food and beverages, and promote the perpetuation of biofilms. Spore-producing bacterial strains that are of particular concern are those in the *Bacillus* and *Clostridium* genera. Both are gram-positive, rod-shaped bacteria that include species that are harmful to humans. *B. anthracis* produces anthrax toxin and *B. cereus* causes food poisoning. *C. botulinum* causes botulism (also known as Botox), *C. difficile* causes diarrhea, *C. perfringens* causes food poisoning, and *C. tetani* causes tetanus. *Bacillus, Paenibacillus,* and *Brevibacillus* bacteria can cause problems in food packaging board products. *Bacillus cereus* is one of the most problematic bacteria because it has been identified as possessing increased resistance to germicidal chemicals used to decontaminate environmental surfaces.

*Bacillus cereus* is frequently diagnosed as a cause of gastrointestinal disorders and has been suggested to be the cause of several food-borne illness outbreaks. Due to its rapid sporulating capacity, *B. cereus* easily survives in the environment. This bacterium can contaminate food directly and indirectly. *B. cereus* can contaminate raw milk directly via feces and soil, and can survive intestinal passage in cows and the pasteurization process. Indirect contamination can come from the presence of *B. cereus* spores in liquid and food packaging. Spores present in materials that come into direct contact with food can cause migration of spores into the food, resulting in spoilage.

Filtration membranes have a tendency to foul during processing. Fouling manifests itself as a decline in flux with time of operation. Flux decline should occur when all operating parameters, such as pressure, flow rate, temperature, and feed concentration are kept constant. Biofouling and the formation of bacterial biofilms are problematic in industrial systems where microorganisms are in liquids. Formation of biofilms can play a role in microbiologically-influenced corrosion. Chemical biocides are typically employed to control biofouling by killing the microorganisms forming the films. However, biocides have difficulty penetrating the extracellular polymeric material in biofilms and removing them from surfaces.

Conventional cleaning and sanitization techniques include the use of or combination of high heat, pH, i.e., very high alkalinity use solutions, or very low pH acidic use solutions, oxidizers, and other biocidal compositions. However, many surfaces cannot tolerate such conditions. For example, membranes used in the manufacture of foods and beverages often have specific limitations with respect to the temperature, pH, and oxidizer concentration at which they can be operated and cleaned due to the material from which they are constructed.

Various methods of cleaning and sanitizing membranes are known and decrease the lifespan of a membrane as a result of damaging the membranes and surrounding equipment that is to be cleaned. For example, an acid treatment might have a corrosive effect on the surfaces of process equipment and on filtration membranes used therein. Also, the rather high temperatures utilized in conventional cleaning methods entail an increase in energy costs. Furthermore, the use of large volumes of acidic inactivation compositions requires later neutralization and proper disposal of the liquid waste. These and other known disadvantages of membrane cleaning systems are known.

Although various agents preventing microbial growth, such as oxidizers, have been used for membrane cleaning there is still a need for an improved method for the removal and reduction of bacterial spores and biofilms without causing significant damage to the membrane material itself. Accordingly, it is an objective of the claimed invention to provide compositions and methods for the prevention and removal of microbial growth on membranes and biofouling of membranes. In particular, it is an object of the invention to provide a method of cleaning membranes, which does not damage the membranes and which mitigates bacterial spore growth and biofilm formation on the membranes.

It is against this background that the present disclosure is made.

SUMMARY

In summary, the present disclosure relates to methods and compositions for reducing and removing biofilm and spores from membranes. Various aspects are described in this disclosure, which include, but are not limited to, the following aspects.

In one aspect, a method of sanitizing a membrane element within a membrane system is provided. The membrane system may be a membrane filtration system in a dairy plant. In some aspects, the method is a clean-in-place method. In some embodiments, the membrane is selected from microfiltration (MF) membranes, ultrafiltration (UF) membranes, nanofiltration (NF) membranes, and reverse osmosis (RO) membranes. A cleaning solution is circulated through the membrane system for about 2 to about 30 minutes at a temperature of about 70° F. to about 125° F. The cleaning solution includes organic acid and surfactant. The organic acid can include a combination of at least two organic acids selected from methyl sulfonic acid, formic acid, citric acid, and lactic acid. In some embodiments, the combination includes citric acid and lactic acid. In some aspects, the cleaning solution includes about 0.1 wt-% to about 1 wt-% organic acid. In some embodiments, the surfactant is an anionic surfactant. In some embodiments, the anionic surfactant is a linear alkyl sulfonate. In some aspects, the surfactant is dodecyl benzene sulfonic acid (DDBSA). In some aspects, the surfactant is included at about 0.01 to about 0.1 wt. %. In some embodiments, the cleaning solution includes a hydrotrope coupler. A sanitizing solution is added to the cleaning solution to produce a boosted antimicrobial solution comprising an oxidant. The oxidant may be a peracid such as peracetic acid or peroctanoic acid, or hydrogen peroxide or ozone. In some aspects, the oxidant is present at about 0.02 wt. % to about 0.15 wt. %. In some embodiments, the sanitizing solution further includes a stabilizer. An exemplary sanitizing solution includes hydrogen peroxide, acetic acid, peracetic acid, and hydroxyethylidene disphosphonic acid in exemplary embodiments. The boosted antimicrobial solution is then circulated through the membrane system for about 1 to about 20 minutes. In some aspects, the method results in at least a 1 log, 2 log, 3 log, or 4 log reduction of bacterial spores on the membrane. In some aspects, the method results in at least a 1 log, 2 log, 3 log, or 4 log reduction of a biofilm, biofoulant, and/or slime forming bacteria. In some embodiments, the combination of organic acid, anionic surfactant, and peracid results in improved chemical compatibility with the membrane as compared to peracid alone, where improved chemical compatibility is shown by protein rejection of UF membranes and/or salt rejection of RO membranes.

In another aspect, a method of cleaning biofilm and bacterial spores from a membrane is described. In some aspects the membrane is a spiral wound membrane. A cleaning solution is prepared that includes at least two organic acids and an anionic surfactant. In some aspects, the organic acids are present at from 0.05 wt-% to 0.5 wt-% and the anionic surfactant is present at from 0.01 wt-% to 0.1 wt-% of the acid cleaning solution. In some embodiments, the cleaning solution includes methyl sulfonic acid, formic acid, sodium xylene sulfonate, and dodecyl benzene sulfonic acid. The cleaning solution is then applied to the membrane for about 2 to about 30 minutes. In some embodiments the sanitizing solution includes peroxyacetic acid, hydrogen peroxide, acetic acid, and hydroxyethylidene diphosphonic acid. A sanitizing solution containing a peracid is added to the cleaning solution. In some aspects the peracid is present at from 0.0001 wt-% to 0.05 wt-% of the sanitizing solution. The combined sanitizing solution and cleaning solution are applied to the membrane for about 1 to about 20 minutes. In some aspects, the first applying step and second applying step occur simultaneously. In some embodiments, the method results in at least 3 log reduction of bacterial spores and biofilm. The method may also result in reduced mineral scaling of the membrane.

In yet another aspect, a clean-in-place method of reducing bacterial spore and biofilm formation on membranes is provided. A cleaning solution is applied to the membrane at a temperature from about 70° F. to about 125° F. The antimicrobial solution includes about 0.05 to about 0.5 wt-% organic acid, about 0.01 to about 0.5 wt-% anionic surfactant, from about 0.04 to about 0.1 wt. % oxidant, and from about 0.001 to about 0.005 wt. % stabilizer.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

Figure 1:
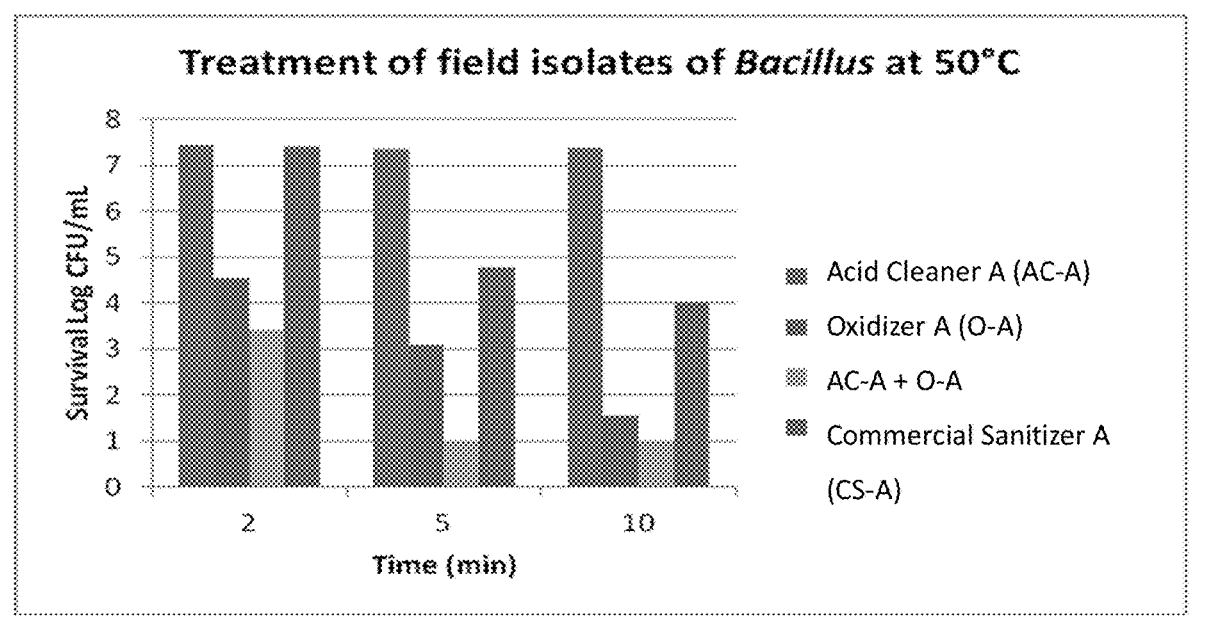

FIG. 1 illustrates a graph comparing the survival of bacterial field isolates following treatment with different combinations of antimicrobial compositions;

DETAILED DESCRIPTION

Figure 2:
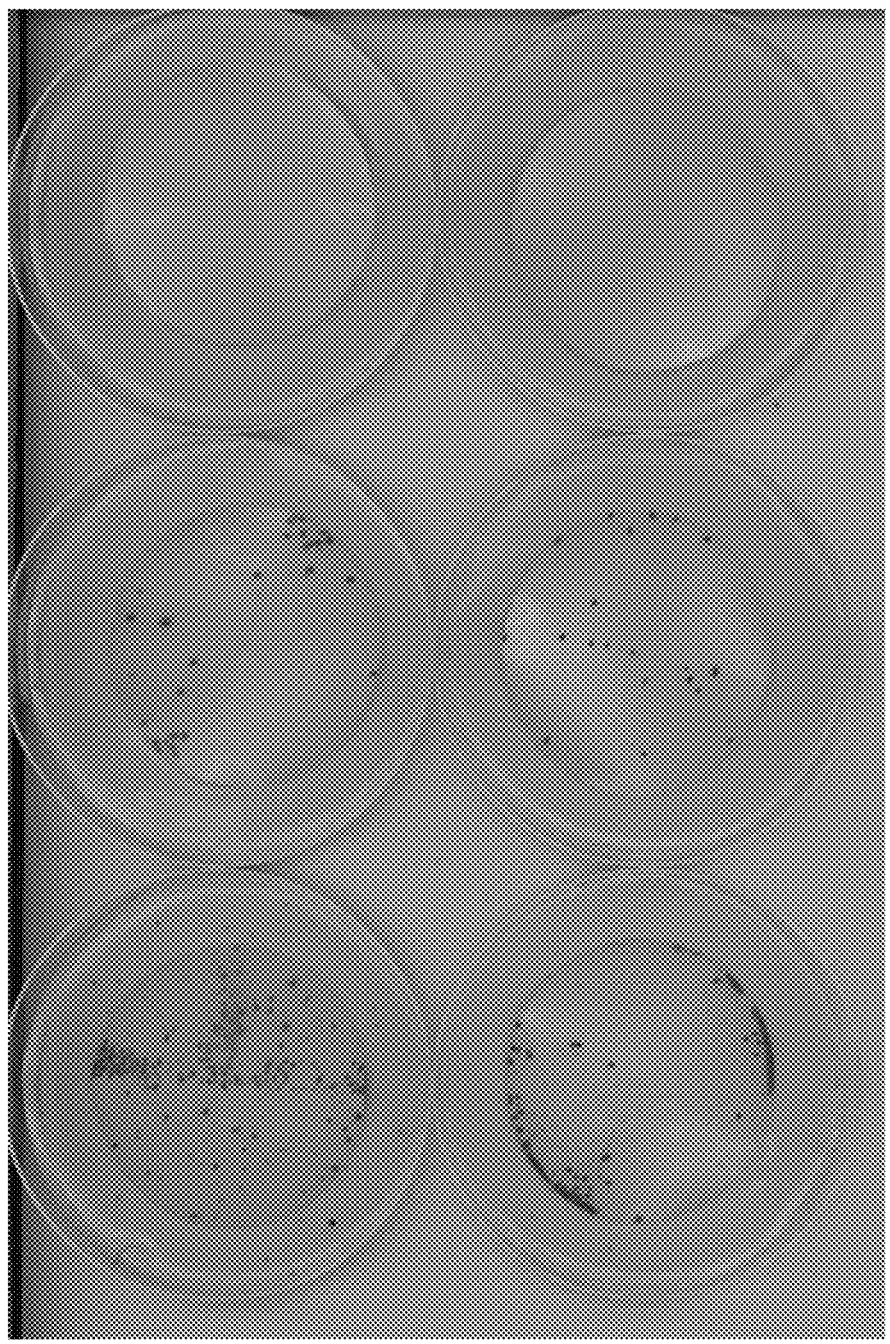
FIG. 2 shows membranes treated with different combinations of antimicrobial compositions to eliminate bacterial spores.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range (e.g. 1 to 5 includes 1, 1.5, 2, 2.75, 3, 3.80, 4, and 5).

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term "actives" or "percent actives" or "percent by weight actives" or "actives concentration" are used interchangeably herein and refers to the concentration of those ingredients involved in cleaning expressed as a percentage minus inert ingredients such as water or salts. The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc. The term "ppm" refers to parts per million.

"Microorganism(s)" means any organism small enough to insinuate itself within, adjacent to, on top of, or attached to a membrane. The definition includes but is not limited to those organisms so small that they cannot be seen without the aid of a microscope, collections or colonies of such small organisms that can be seen by the naked eye but which comprise a number of individual organisms that are too small to be seen by the naked eye, as well as one or more organisms that can be seen by the naked eye. The definition also includes but is not limited to any organism whose presence, in some way impairs the operation of a membrane; noncellular or unicellular (including colonial) organisms; all prokaryotes (and certain eukaryotes); and bacteria (including cyanobacteria), spores, lichens, fungi, protozoa, virinos, viroids, viruses, phages, and some algae. As used herein, the term "microbe" is synonymous with microorganism.

As used herein, the term "cleaning" refers to a method used to facilitate or aid in soil removal, bleaching, microbial population reduction, and any combination thereof.

As used herein, the term "disinfectant" refers to an agent that kills all vegetative cells including most recognized pathogenic microorganisms.

The term "generally recognized as safe" or "GRAS," as used herein refers to components classified by the Food and Drug Administration as safe for direct human food consumption or as an ingredient based upon current good manufacturing practice conditions of use, as defined for example in 21 C.F.R. Chapter 1, § 170.38 and/or 570.38.

As used herein, the term "sanitizer" refers to an agent that reduces the number of bacterial contaminants to safe levels as judged by public health requirements. In an embodiment, sanitizers for use in this invention will provide at least a 3 log reduction and more preferably a 5-log order reduction.

As used in this invention, the term "sporicide" refers to a physical or chemical agent or process having the ability to cause greater than a 90% reduction (1-log order reduction) in the population of spores of *Bacillus cereus* or *Bacillus subtilis* within 10 seconds at 60° C. In certain embodiments, the sporicidal compositions of the invention provide greater than a 99% reduction (2-log order reduction), greater than a 99.99% reduction (4-log order reduction), or greater than a 99.999% reduction (5-log order reduction) in such population within 10 seconds at 60° C.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbiostatic. A sanitizer and a disinfectant are, by definition, agents which provide antimicrobial or microbiocidal activity. In contrast, a preservative is generally described as an inhibitor or microbiostatic composition.

The methods, systems, apparatuses, and compositions of the present invention may comprise, consist essentially of, or consist of the components and ingredients of the present invention as well as other ingredients described herein. As used herein, "consisting essentially of" means that the methods, systems, apparatuses and compositions may include additional steps, components or ingredients, but only if the additional steps, components or ingredients do not materially alter the basic and novel characteristics of the claimed methods, systems, apparatuses, and compositions.

In general, the present disclosure relates to compositions and methods for removing and reducing bacterial spores and biofilm formation on membrane surfaces. A combination treatment of an acid cleaner and an oxidizer sanitizer are applied to membranes to remove bacterial spores and biofilms. The treatment can be applied in a clean-in-place (CIP) process or as part of a soaking process. In some embodiments, the methods and compositions are applied to membranes used in the food industry, the beverage industry, the biotechnology industry, the pharmaceutical industry, the chemical industry, and the water purification industry. In the case of the food and beverage industries, the methods and compositions can be used on membranes as part of the production of water, milk, whey, fruit juice, beer, and wine. The membranes can include microfiltration (MF) membranes, ultrafiltration (UF) membranes, nanofiltration (NF) membranes, and reverse osmosis (RO) membranes. In some embodiments, the membranes may be polymeric, ceramic, or stainless steel. In some embodiments, the membrane is configured as a spiral wound membrane, hollow fiber membrane, tubular membrane, or a plate and frame flat sheet membrane. Membranes are utilized for a variety of separation methods to convert a mixture of a substance(s) into distinct mixtures, at least one of which is enriched in one or more of the mixture's constituents. The membranes that can be treated according to the invention include any membranes that are designed for periodic cleaning, and are often utilized in various applications requiring separation by filtration.

The present disclosure describes a combination of cleaning solutions that are utilized to clean and sanitize membranes. As referred to herein, the removing of microorganisms, biofilm and mineral deposits refers to the reduction in microorganisms, biofilm and mineral deposits on a membrane surface, the disbursement of microorganisms, biofilm and mineral deposits on a membrane surface, and/or the inactivating of microorganisms, biofilm and mineral deposits on a membrane surface.

Membrane Filtration Cleaning Compositions

The present disclosure describes the use of a two-part cleaning system that synergistically removes and reduces bacterial spores and biofilms from membranes without significant negative impact to the performance or integrity of the membranes. In some aspects, the cleaning system also aids in de-scaling of the membranes. The two-part cleaning system utilizes an acid cleaning solution and an oxidizer sanitizing solution. The two parts of the system can be applied to the membrane at the same time or sequentially.

The acid cleaning solution includes at least an organic acid and a surfactant. In some embodiments, the acid cleaning solution includes at least two organic acids and an anionic surfactant. The oxidizer sanitizing solution includes at least an oxidizer. In some embodiments, the oxidizer sanitizing solution includes at least a peracid.

Anionic Surfactants

In some aspects, an anionic surfactant is included in the acid cleaning solution. The surfactant improves the surface activity of the cleaning solution on the membrane surface. In some embodiments, the anionic surfactant can also help prevent or reduce corrosion of the acid cleaning system on the membrane system. Anionic surfactants are surface active substances having a negative charge on the hydrophobe or have a hydrophobic section that carries no charge unless the pH is elevated to neutrality or above (e.g. carboxylic acids). Carboxylate, sulfonate, sulfate, and phosphate are the polar (hydrophilic) solubilizing groups found in anionic surfactants. Anionic surfactants useful in the acid cleaning solution include alkyl sulfates, alkyl sulfonates, alkane sulfonates, linear and branched primary and secondary alkyl sulfonates, the aromatic sulfonates with or without substituents, linear alkyl benzene or naphthalene sulfonates, secondary alkane sulfonates, alkyl ether sulfates or sulfonates, alkyl phosphates or phosphonates, and mixtures thereof. Specific examples include sodium alkane sulfonate, alpha olefin sulfonate, sodium lignosulfonate, sodium lauryl ether sulfate, sodium lauryl sulfate, sodium dioctyl sulfosuccinate, sodium dodecyl benzene sulfonic acid, sodium xylene sulfonate, sulfonated diphenyl oxide surfactants sold under the tradename DOWFAX including DOWFAX C6L, 3B2, 8390, and 2A1, capryleth-9 carboxylic acid/hexeth-4 carboxylic acid (such as AKYPO LF4), sodium methyl 2-sulfolaurate (such as ALPHASTEP PC48), sarcosinates, and mixtures thereof.

In preferred aspects, the anionic surfactant comprises a linear alkyl sulfonate, dodecyl benzene sulfonic acid (DDBSA), sodium xylene sulfonate, or a combination thereof.

Organic Acids

The acid cleaning solution includes at least one organic acid. In exemplary embodiments, the acid cleaning solution includes at least two organic acids. Suitable organic acids include methane sulfonic acid, ethane sulfonic acid, propane sulfonic acid, butane sulfonic acid, xylene sulfonic acid, benzene sulfonic acid, formic acid, acetic acid, picolinic acid, dipicolinic acid, citric acid, lactic acid, formic acid, acetic acid, propionic acid, butyric acid, valeric acid, caproic acid, gluconic acid, itaconic acid, trichloroacetic acid, benzoic acid and mixtures thereof. Preferably, the organic acids are selected from citric acid, lactic acid, formic acid, and methyl sulfonic acid. In some embodiments, the organic acids include a combination of citric acid and lactic acid. In some embodiments, the organic acids include a combination of formic acid and methyl sulfonic acid.

The pH of the acid cleaning solution in a concentrate is preferably about 0 to about 3. The pH of the acid cleaning composition in a use solution is preferably about 1 to about 3. A use solution pH below 1.8 can be detrimental to the membrane integrity and performance.

Oxidizer

The oxidizer sanitizing solution includes an oxidizer. In some embodiments the oxidizer is a peracid (peroxycarboxylic acid). In some embodiments, the oxidizer is a combination of oxidizing agent, carboxylic acid, and stabilizer, which produces a peroxycarboxylic acid.

Many oxidizing agents can be used for generating peroxycarboxylic acids. Suitable oxidizing agents, in addition to hydrogen peroxide, include inorganic and organic peroxides, such as, salts of perborate, percarbonate, and persulfate, percarbonic acid, and ozone. In preferred embodiments, the oxidizing agent is hydrogen peroxide.

Suitable peracids or peroxycarboxylic acids include peroxyacetic acid, peroxyoctanoic acid, peroxyformic acid, peroxypropionic acid, peroxybutyric acid, peroxyvaleric acid, peroxyhexanoic acid, peroxyheptanoic acid, peroxynonanoic acid, peroxydecanoic acid, and mixtures thereof. In preferred embodiments, the peracid is peroxyacetic acid.

Stabilizer

In some embodiments, the oxidizer sanitizing solution includes a stabilizer. Stabilizers, particularly those suitable for stabilizing peroxygen compounds or peroxycarboxylic acids, include organic chelating compounds that sequester metal ions in solution, particularly most transition metal ions, which would promote decomposition of any peroxygen compounds therein. Typical complexing agents include organic amino- or hydroxy-polyphosphonic acid complexing agents (either in acid or soluble salt forms), carboxylic acids, hydroxycarboxylic acids, aminocarboxylic acids, or magnesium or tin compounds (e.g., tin oxalate).

Chelating agents or sequestrants generally useful as stabilizers in the present compositions include salts or acids of (expressed in acid form) dipicolinic acid, picolinic acid, gluconic acid, quinolinic acid, and alkyl diamine polyacetic acid-type chelating agents such as ethylenediamine tetraacetic acid (EDTA), hydroxyethylethylethylene diamine triacetic acid (HEDTA), and ethylene triaminepentaacetic acid, acrylic and polyacrylic acid-type stabilizing agents, phosphonic acid, and phosphonate-type chelating agents among others. Preferable sequestrants include phosphonic acids and phosphonate salts including 1-hydroxy ethylidene-1,1-diphosphonic acid $(CH_3C(PO_3H_2)_2OH)$(HEDP); ethylenediamine tetrakis methylenephosphonic acid (EDTMP); diethylenetriamine pentakis methylenephosphonic acid (DTPMP); cyclohexane-1,2-tetramethylene phosphonic acid; amino[tri(methylene phosphonic acid)]; (ethylene diamine[tetra methylene-phosphonic acid)]; 2-phosphene butane-1,2,4-tricarboxylic acid; as well as the alkyl metal salts, ammonium salts, or alkyloyl amine salts, such as mono, di, or tetra-ethanolamine salts. In preferred embodiments the stabilizer is HEDP.

In some embodiments, a coupler, or hydrotrope, is included in the oxidizer sanitizing solution. In one embodiment, the coupler is sodium xylene sulfonate.

In some embodiments, the cleaning or antimicrobial compositions do not include materials that may be detrimental to membrane surfaces. For example, in some embodiments, the cleaning or antimicrobial compositions are free or substantially free of surfactants other than anionic surfactants. Membrane surfaces are often negatively charged and including a cationic or nonionic surfactant can have negative reactions with the membrane surface. In some embodiments, the cleaning or antimicrobial compositions are free or substantially free of oxidizers other than peracids, hydrogen peroxide, or ozone. In some embodiments, the cleaning or antimicrobial compositions are free or substantially free of chlorine. Chlorine and other oxidizers may negatively affect the integrity or performance of the membrane. In some embodiments, the cleaning or antimicrobial compositions are free or substantially free of inorganic acids. Again, inorganic acids may negatively affect the integrity or performance of the membrane.

Tables 1 and 2 below show exemplary concentration ranges for the various components in a concentrate and use solution composition.

TABLE 1

Exemplary Formulations of Concentrate Components

| Component | Concentration (wt-%) | Concentration (wt-%) | Concentration (wt-%) |
|---|---|---|---|
| Acid Cleaner | | | |
| Organic Acid | about 10-about 40 | about 15-about 25 | about 18-about 22 |
| Anionic Surfactant | about 1-about 10 | about 3-about 7 | about 4-about 6 |
| Water | about 50-about 90 | about 60-about 80 | about 65-about 75 |
| Coupler | about 0-about 20 | about 1-about 15 | about 6-about 10 |
| Oxidizer Sanitizer | | | |
| Acid | about 5-about 25 | about 8-about 15 | about 10-about 12 |
| Oxidant | about 75-about 90 | about 80-about 88 | about 82-about 86 |
| Stabilizer | about 0.5-about 2.5 | about 1-about 2 | about 1.5-about 1.7 |
| Water | about 1-about 10 | about 2-about 5 | about 2.5-about 3 |

TABLE 2

Exemplary Formulations of Use Components

| Component | Concentration (wt-%) | Concentration (wt-%) | Concentration (wt-%) |
|---|---|---|---|
| Acid Cleaner | | | |
| Organic Acid | about 0.05-about 1 | about 0.1-about 0.5 | about 0.15-about 0.3 |
| Anionic Surfactant | about 0.01-about 0.1 | about 0.025-about 0.075 | about 0.04-about 0.05 |
| Water | about 90-about 99.99 | about 99-about 99.9 | about 99.6-about 99.8 |
| Coupler | about 0-about 0.25 | about 0.01-about 0.15 | about 0.07-about 0.09 |
| Oxidizer Sanitizer | | | |
| Acid | about 0.001-about 0.03 | about 0.005-about 0.025 | about 0.01-about 0.02 |
| Oxidant | about 0.02-about 0.15 | about 0.04-about 0.1 | about 0.06-about 0.08 |
| Stabilizer | about 0.0005-about 0.01 | about 0.001-about 0.005 | about 0.002-about 0.003 |
| Water | about 95-about 99.999 | about 98-about 99.99 | about 99.5-about 99.95 |
| Peracid | about 0.0001-about 0.05 | about 0.005-about 0.025 | about 0.01-about 0.02 |

Methods of Sanitizing/Cleaning Membranes

In an aspect, a combination of an acid cleaning solution and an oxidizer sanitizing solution are used to synergistically clean and sanitize membranes that are prone to biofilm formation and contamination with bacterial spores. In some embodiments, the acid cleaning solution is first applied to a membrane to clean the membrane. The oxidizer sanitizing solution is then combined with the acid cleaning solution to produce a boosted antimicrobial solution. This boosted solution is then circulated in the membrane to sanitize the membrane. The pressure of the membrane system can be modified to increase or decrease the permeation rate of this combination cleaning solution if there are cleaning issues on the permeate side of a membrane system.

In another aspect, an acid cleaning solution and an oxidizer sanitizing solution are combined before application to membranes. The acid cleaning solution and oxidizer sanitizing solution combine to form a boosted antimicrobial solution that is packaged for use in a single step.

In some embodiments, the method is a clean-in-place method applied to a membrane filtration system. In such embodiments, the acid cleaning solution and oxidizer sanitizing solution are circulated through the membrane filtration system.

In an exemplary embodiment, a cleaning solution is prepared comprising organic acid and surfactant. The cleaning solution is circulated through a membrane system for about 2 to about 60 minutes, about 2 to about 30 minutes, or about 2 to about 15 minutes. In some embodiments, the membrane may be allowed to soak in the cleaning solution for up to about 30 days, or about 0.5 to about 15 days, or about 1 to 7 days, or 1 to 3 days. A sanitizing solution is added to the cleaning solution to produce a boosted antimicrobial solution, where the sanitizing solution comprises an oxidizer. The antimicrobial solution is circulated through the membrane system for about 1 to about 30 minutes, about 1 to about 20 minutes, about 1 to about 10 minutes or about 5 to about 10 minutes. In some aspects, the method results in at least a 1 log, at least a 2 log, or at least a 3 log reduction of bacterial spores on the membrane. In some embodiments, the method results in at least a 1 log, at least a 2 log, or at least a 3 log reduction of a biofilm, biofoulant, and/or slime forming bacteria.

In some embodiments, the cleaning solution and antimicrobial solution are circulated in the membrane system at a temperature of about 70° F. to about 125° F.

The methods and compositions described above provide a surprisingly synergistic effect over prior membrane treatments. The combination of organic acids, anionic surfactant, and peracid results in improved chemical compatibility with the membrane as compared to peracid alone. Use of CIP treatments that exhibit good chemical compatibility with membranes result in membranes that remain viable for longer periods of time despite exposure to cleaning compositions.

Chemical compatibility of membranes are assessed by determining the membrane rejection rates. Rejection rates of membranes indicate how well the membrane is performing to filter a particular substance. For UF membranes, a high rejection rate indicates that the membrane is filtering protein effectively. Low rejection rates for UF membranes indicate that the membrane has been compromised and is no longer effectively filtering out proteins from solution. In the case of RO membranes, high rejection rates indicate that the membrane is filtering salt properly, while low rejection rates indicate that the membrane is not filtering salt properly.

In some embodiments, the methods are effective for removing not only bacterial spores and biofilms, but for descaling mineral deposits on membranes. Embodiments in which the acid cleaning solution includes formic acid and methyl sulfonic acid in addition to an anionic surfactant are more effective at removing mineral deposits from membranes.

EXAMPLES

The following concentrates are used in the examples below.

TABLE 3

Acid Cleaner A (AC-A)

| Wt-% | Description | Function |
|---|---|---|
| 75 | Water | Solvent |
| 10 | Citric Acid (Anhydrous) | Acidulant |
| 10 | Lactic Acid, 88% | Acidulant |
| 5 | Dodecyl Benzene Sulfonic Acid (DBSA), 96% | Surfactant |

TABLE 4

Acid Cleaner B (AC-B)

| Wt-% | Description | Function |
|---|---|---|
| 67.82 | Water | Solvent |
| 14.67 | Methyl Sulfonic Acid | Acidulant |
| 5 | Formic Acid, 85% | Acidulant |
| 8.4 | Sodium Xylene Sulfonate (SXS), 40% | Coupler |
| 4.11 | Dodecyl Benzene Sulfonic Acid (DBSA), 96% | Surfactant |

TABLE 5

| Oxidizer A (O-A) | | |
|---|---|---|
| Wt-% | Description | Function |
| 84.3 | Hydrogen peroxide 35% Peracid Grade DRM | Antimicrobial |
| 1.6 | Hydroxyethylidene Diphosphonic acid, 60%, Peracid gr. | Stabilizer |
| 11.2 | Glacial Acetic Acid (peracid grade) IBC | Antimicrobial |
| 2.9 | Water, Deionized (peracid grade) TNK | Solvent |

TABLE 6

| Commercial Sanitizer A (CS-A) | | |
|---|---|---|
| Wt-% | Description | Function |
| 10-30 | Acetic acid | Antimicrobial |
| 6.9 | Hydrogen Peroxide | Oxidizer |
| 1-5 | Secondary Alkanesulphonates | Surfactant |
| 4.4 | Peroxyacetic Acid | Antimicrobial |
| 3.3 | Octanoic Acid | Antimicrobial |

Example 1

First, an in-vitro test was performed to compare the performance of antimicrobial solutions for reducing the survival of *Bacillus* sp. field isolate.

Figure 3:
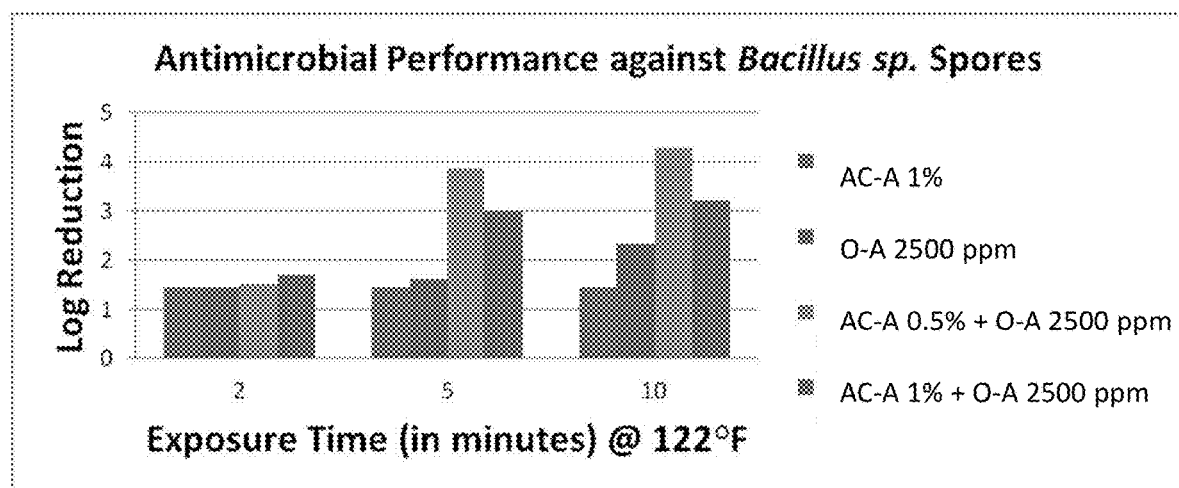
FIG. 3 illustrates a graph comparing the antimicrobial performance of different combinations of antimicrobial compositions against bacterial spores.

The bacterial samples were combined with dilutions of each cleaning solution. The formulas in Tables 3-5 were diluted to 1% solutions and the formula in Table 6 was diluted to a 0.25% solution. The samples were then neutralized to stop the chemical process. The samples were plated onto microbiological media to incubate and count for survivors. The samples were incubated at 50° C. for 2, 5, or 10 minutes.

The results are shown in FIG. 1. The survival log of *Bacillus* sp. is graphed in CFU/mL against time (minutes). The results show that Acid Cleaner A (AC-A) is not as effective as the Commercial Sanitizer A (CS-A) for reducing bacterial survival. However, Oxidizer A (O-A) showed improved efficacy over CS-A. Surprisingly, a combination of O-A with AC-A resulted in even better antimicrobial efficacy with only a 1 CFU/mL survival rate after 10 minutes.

Example 2

Next, the experimental formulations were tested and compared for efficacy of spore removal from membranes. First, spore isolates were diluted with sterile distilled water to produce a solution having a final concentration of $10^4$ CFU/mL of mixture of *Bacillus* spore field isolates. 6 ultrafiltration (UF) polyethersulfone (PES) membranes (Spirapro, KOCH, Wilmington, Mass.) were soaked in the $10^4$ CFU/mL spore solution for 24 hours. The membranes were rinsed using the dipping method and were placed into individual sterile centrifuge tubes. A combination treatment of AC-A and O-A was applied at 2500 ppm to two of the membranes in the tubes for 5 minutes. CS-A was applied at 2600 ppm to two of the membranes for 5 minutes as a comparison. Deionized water (DI) was used as a control on two membranes. Some membranes were stored wet in a preservative solution and others were tested dry.

The results are displayed in Table 7 and FIG. 2. Visual grading was done on a scale of 1-5, with 5 having the appearance of the greatest number of spores.

TABLE 7

| Spore Removal | | | | | | | | | | | | |
|---|---|---|---|---|---|---|---|---|---|---|---|---|
| | CS-A @ 2600 ppm | | | | | | AC-A (1% v/v) + O-A @ 2500 ppm | | | | | |
| | Visual Grading | | | Image Analysis (% Spores Removed) | | | Visual Grading | | | Image Analysis (% Spores Removed) | | |
| Temp: 50° C. | Wet | Dry | Ave | Wet | Dry | Ave | Wet | Dry | Ave | Wet | Dry | Ave |
| 5 minutes | 3 | 2 | 2.5 | 76% | 84% | 80% | 1 | 1 | 1 | 100% | 100% | 100% |
| Control | 5 | 5 | 5 | 0% | 0% | 0% | 5 | 5 | 5 | 0% | 0% | 0% |

As can be seen in FIG. 2, no visible spores are growing on the plate treated with AC-A+O-A. Compared to CS-A, the combination of AC-A+O-A was much more effective at spore removal. This indicated that antimicrobial performance of a standard hydrogen peroxide, acetic acid, and peracetic acid solution was enhanced by addition of DDBSA, citric acid, and lactic acid. These results held true for both wet and dry samples.

Example 3

The antimicrobial performance of the example formulas were tested against *Bacillus* sp. spores. The samples were exposed to the example formulas for 2, 5, or 10 minutes at 122° F. The suspension method described above in Example 1 was utilized. Samples were observed to determine the amount of time required to achieve a log reduction in organisms.

FIG. 3 illustrates the results of a comparison of AC-A at 1% dilution, O-A at 2500 ppm, AC-A at 0.5% dilution+O-A at 2500 pm, and AC-A at 1% dilution+O-A at 2500 ppm. While both combinations of AC-A+O-A were more effective than either AC-A or O-A alone, the combination of 0.5% AC-A+2500 ppm O-A was the most effective at eliminating *Bacillus* sp. spores. As can be seen in the chart of FIG. 3, 10 minutes of exposure to AC-A 0.5%+O-A 2500 ppm at 122° F. resulted in over a 4 Log reduction in the amount of spores present. This combination and concentration of solutions was more effective than AC-A at 1%+O-A 2500 ppm, which results in a 3 Log reduction of spores after 10 minutes. Both concentrations of AC-A combined with O-A were still more effective for antimicrobial performance against *Bacillus* sp. spores than AC-A or O-A alone. This comparison illustrates the synergy between the AC-A and O-A solutions.

Example 4

Figure 4:
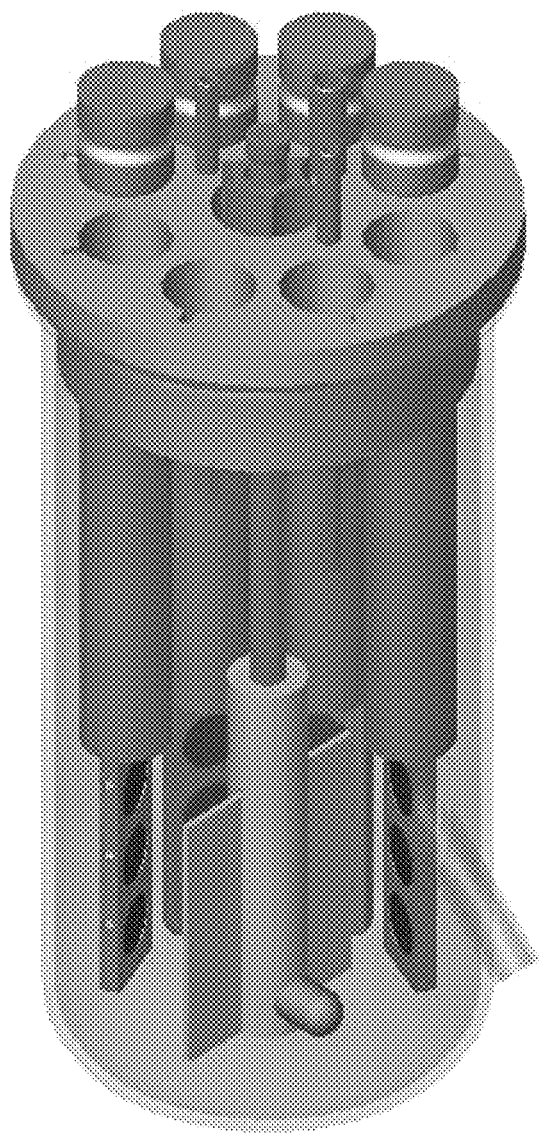
FIG. 4 is a schematic diagram of a CDC biofilm reactor.

The experimental formulas were also tested for efficacy in removing biofilm from PES UF membrane surfaces using the Centers for Disease Control (CDC) biofilm reactor (BioSurface Technologies Corporation, Bozeman, Mont.) illustrated in FIG. 4. The test method was based upon the US EPA Standard Operating Procedure for Single Tube Method for Measuring Disinfectant Efficacy Against Biofilm Grown in the CDC Biofilm Reactor.

Bacterial strains used were *Pseudomonas aeruginosa* and a field isolate of *Bacillus* sp. The bacterial strains were grown in tryptic soy broth (TSB) growth media and pasteurized 2% milk. The bacterial cultures were grown on tryptone glucose extract (TGE) agar. Then 1 loop of *Pseudomonas aeruginosa* pure culture was inoculated into 100 mL of 1% TSB and incubated for 24 hours at 35° C. This was repeated for the *Bacillus* sp. spores. Pieces of PES UF membrane were secured to the porous media holders. The membranes were then treated with a typical clean-in-place solution before using for biofilm development. 500 mL of solution was agitated with a 1.5" stir bar at 200 rpm. The steps of the membrane conditioning process are summarized in Table 2.

TABLE 8

Membrane conditioning processes

| Step | Product | Conc. | Time | Temp (° F.) |
| --- | --- | --- | --- | --- |
| DI Water Rinse | DI Water | Neat | 10 | 75 |
| Chlorinated Alkaline | AC-A 110 + Chlorine | pH 11 + 180 ppm | 30 | 120 |
| DI Water Rinse | DI Water | Neat | 10 | 75 |

The media membrane holders were then placed into the CDC biofilm reactor. 1 mL of the test organisms were inoculated into the biofilm reactor with growth media. Biofilms were generated on the membranes after 24 hours of no growth media cross flow using 1% TSB at 25° C. with stirring at 180 rpm followed by 24 hours of a continuous supply of pasteurized 2% milk growth media flowing through the CDC biofilm reactor at 10.3 mL/min. The media membrane holders were then removed from the biofilm reactor and rinsed to remove planktonic cells. Each membrane holder was held vertically over a separate 50 mL conical tube containing 30 mL Standard Method Dilution Water (SMDW). The holders were immersed with continuous motion into the SMDW and immediately removed.

The membranes were removed from the holders and cut in half. Half of the membrane pieces were rinsed for 10 minutes in a 4 mL sterile deionized (DI) water sample. The resulting water solution was then vortexed for 30 seconds, sonicated for 30 seconds, and vortexed again for 30 seconds. The resulting solution was serially diluted in sterile DI water and plated onto TGE plating media. The remaining half of the membrane pieces were exposed to sanitizer solutions for 10 minutes. Then neutralizing solution was added to each sample to stop the chemical reaction. The resulting solution was serially diluted in sterile DI water and plated onto TGE plating media for incubation.

Figure 5:
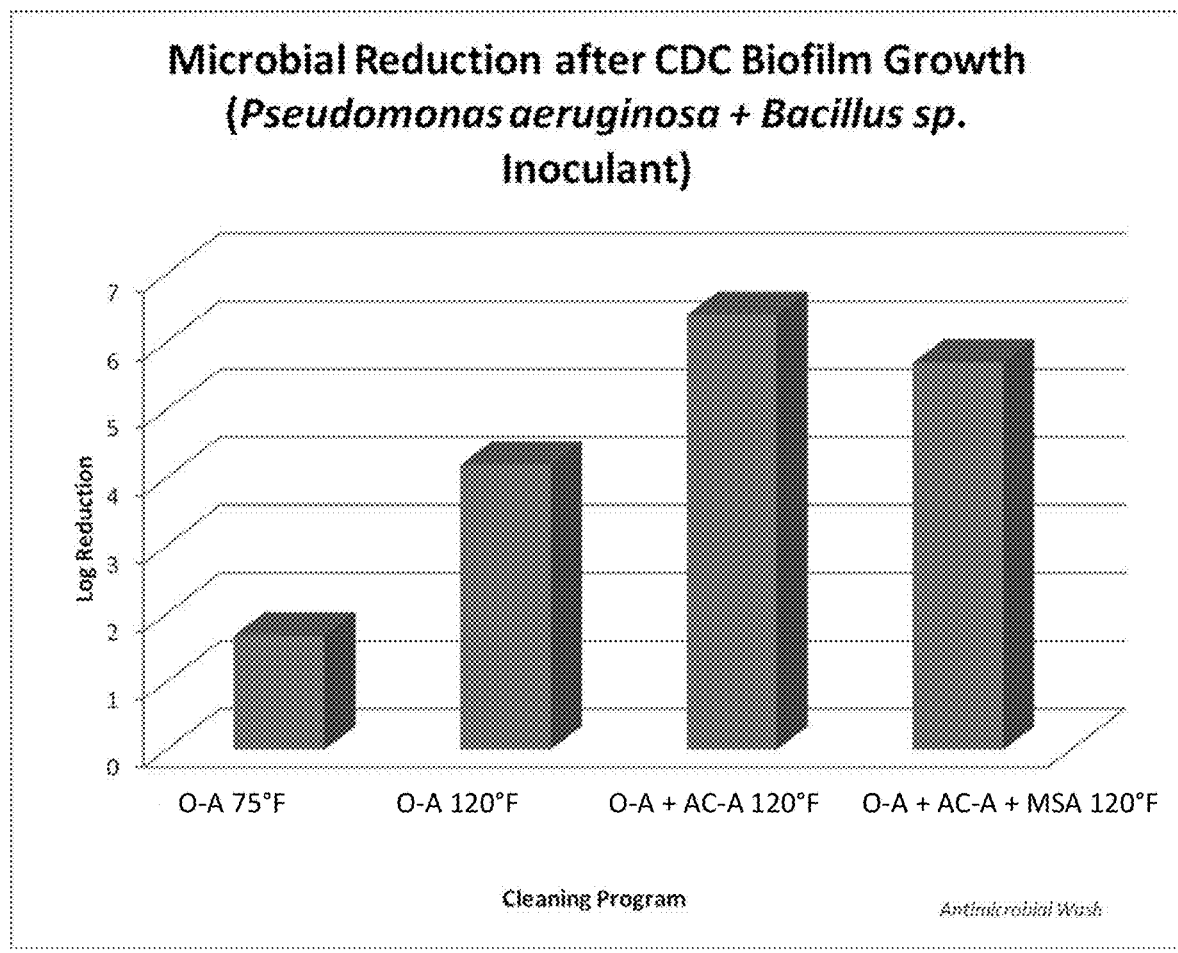
FIG. 5 illustrates a graph comparing the performance of different combinations of antimicrobial compositions for reducing biofilm on membranes.

FIG. 5 illustrates the results of the biofilm testing on membranes. The log reduction in biofilm growth was recorded and graphed. As is shown in the graph, treating the membrane at a temperature of 120° F. is more effective than 75° F. with O-A alone. The combination of O-A with AC-A was more effective at reducing biofilm than O-A alone. Additionally, O-A+AC-A with the addition of methyl sulfonic acid (MSA) was less effective than O-A with AC-A, but more effective than O-A alone.

Example 5

Material compatibility testing was performed to observe effects on membrane rejection rates which is an indication of degradation to the membrane surface. Testing was performed on both PES UF membrane material and RO membranes. The samples were soaked for 5.7 days. Based upon 15 minutes of CIP contact per day, this equates to 1.5 years of daily exposure to the chemistry.

Figure 6:
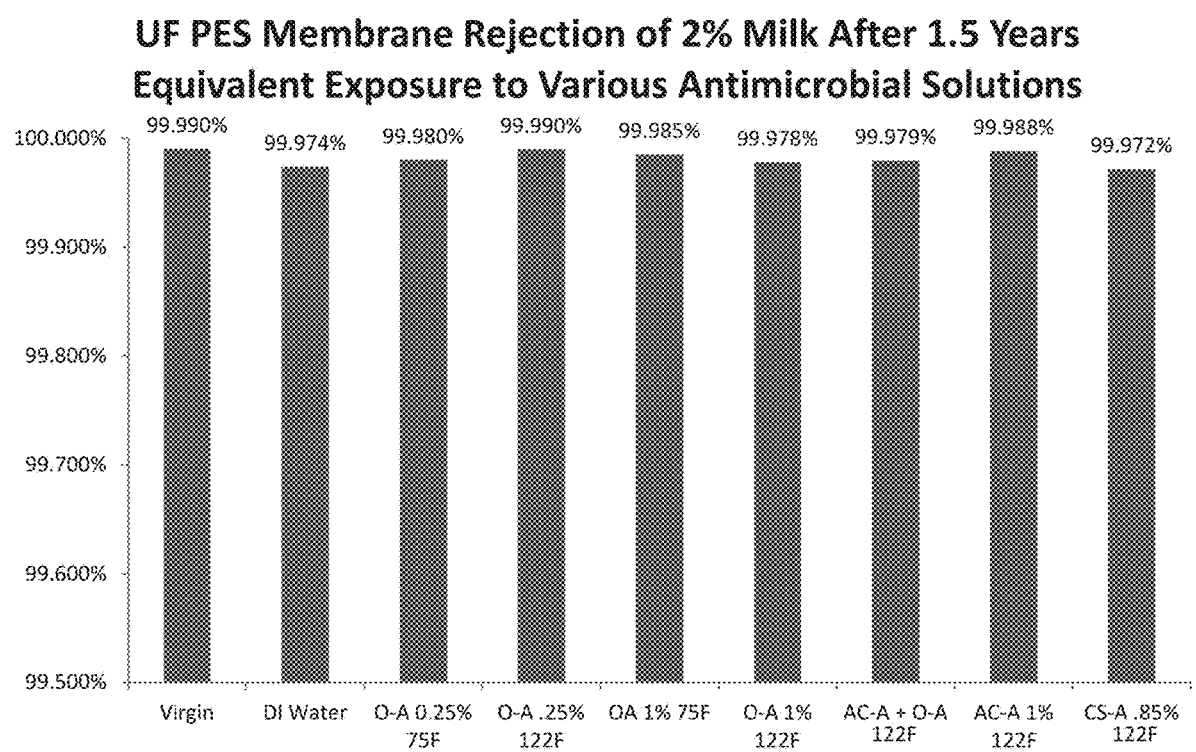
FIG. 6 illustrates a graph comparing PES membrane rejection after treatment with different combinations of antimicrobial compositions.

The PES UF membranes were examined for rejection of milk proteins, where the percent rejection equals ((protein in permeate−protein in milk feed)/protein milk feed)*100. The graph in FIG. 6 shows that long term chemical exposure (replicate 1.5 years) did not result in decreased rejection rates for UF PES membranes, which is an indication of material compatibility.

Figure 7:
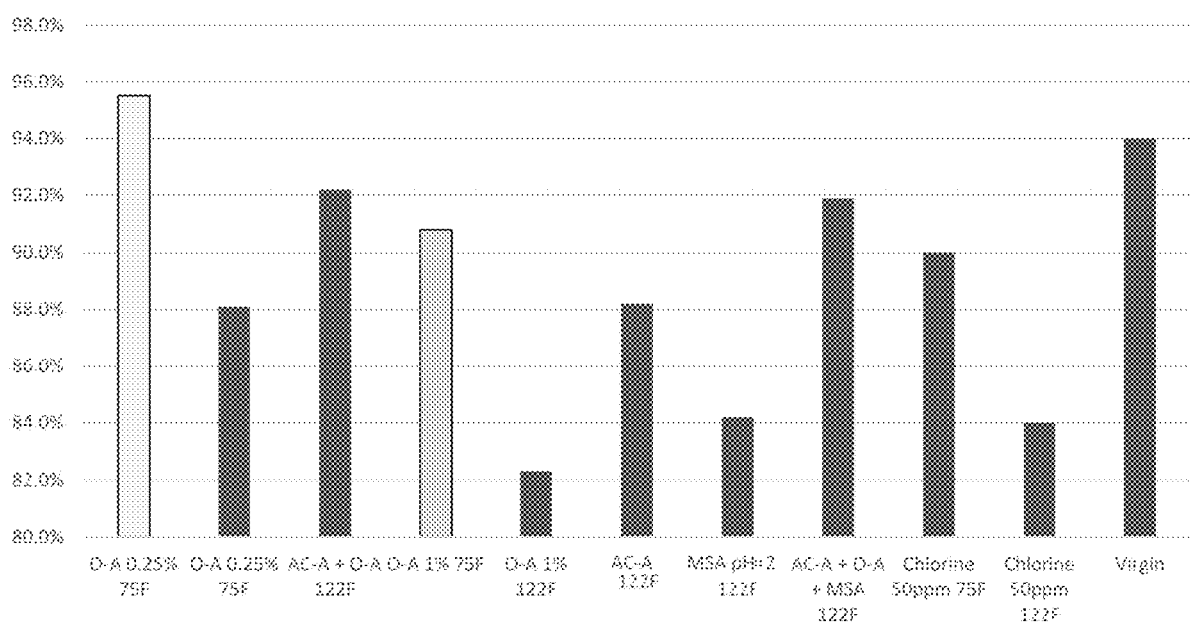
FIG. 7 illustrates a graph comparing RO membrane rejection after treatment with different combinations of antimicrobial compositions.

The RO membranes were tested for rejection using conductivity with 2% NaCl as the feed solution. The percent rejection=((conductivity of permeate−conductivity of NaCl feed)/conductivity of NaCl feed)*100. The results are shown in FIG. 7. Surprisingly, long term chemical exposure (just over a year for all samples except for O-A 0.25% 75F and O-A 1% 75F, which were tested for the equivalent of 48 days) using the test chemical composition of AC-A+O-A had much higher rejection rates than those observed when using an acetic acid, hydrogen peroxide, and peroxyacetic acid solution alone. The finding may be evidence of a RO compatible oxidizing solution that can be used at elevated temperatures.

Example 6

In addition to the antimicrobial and compatibility benefits of the chemical composition, testing indicated that a chemical composition consisting of DDBSA, citric acid, and lactic acid (AC-A) interferes with *Bacillus* sp. spore isolates ability to adhere or grow on PES UF membrane surfaces and to a lesser degree RO membrane surfaces. The purpose of this study was to determine *Bacillus* sp. *mesophilic* spore field isolate adhesion properties with RO and UF (PES) membrane surfaces when the membrane and spores were soaked in DI water vs an AC-A 1% solution. A description of the soaking conditions for each membrane disk are provided in Table 9. Membranes 9-12 served as controls.

TABLE 9 membrane soaking conditions

| Membrane Disk # | Membrane Soak Solution | Spore Solution | Membrane Type |
|---|---|---|---|
| 1 | AC-A 1% | Spores diluted with DI water | UF & RO |
| 2 | AC-A 1% | Spores diluted with DI water | UF & RO |
| 3 | DI Water | Spores diluted with DI water | UF & RO |
| 4 | DI Water | Spores diluted with DI water | UF & RO |
| 5 | AC-A 1% | Spores diluted with 1% AC-A | UF & RO |
| 6 | AC-A 1% | Spores diluted with 1% AC-A | UF & RO |
| 7 | DI Water | Spores diluted with 1% AC-A | UF & RO |
| 8 | DI Water | Spores diluted with 1% AC-A | UF & RO |
| 9 | AC-A1% | DI Water + No Spores | UF & RO |
| 10 | AC-A1% | AC-A1% + No Spores | UF & RO |
| 11 | DI Water | DI Water + No Spores | UF & RO |
| 12 | DI Water | AC-A1% + No Spores | UF & RO |

Two dilute milk spore isolate solutions were produced with field isolate mesophilic *Bacillus* sp. spores. One solution used sterile DI as diluent while the other solution used 1% AC-A solution as diluent. 1 inch diameter membrane disks were stored in AC-A solution and then rinsed in DI water before use. 6 PES and 6 RO membrane disks were soaked in AC-A (1% v/v) solution for 72 hours. 6 PES and 6 RO membrane disks were soaked in DI water solution for 72 hours as a control. After soaking, the membranes were placed into 25 mL plastic (Nalgene) containers. 10 mL of the appropriate spore solution was placed into respective Nalgene containers and the membrane disks were allowed to soak for 24 hours. The membrane disks were then removed from the spore solutions and rinsed with DI water.

Each membrane disk was plated. 1 mL TTC dye was added to 100 mL TGE agar, which was then applied in a thin layer to petri dishes and allowed to dry. The membranes were placed on the dried plates and more agar was added until the membranes were covered. The membranes then incubated at 35° C. for 48 hours. The membranes were visually graded after 48 hours on a scale of 1-5, with 1 being no visual spores and 5 being control membranes.

Figure 8A:
FIGS. 8A-8B shows RO and UF membranes treated with different combinations of antimicrobial compositions to eliminate bacterial spores.
Figure 8A:
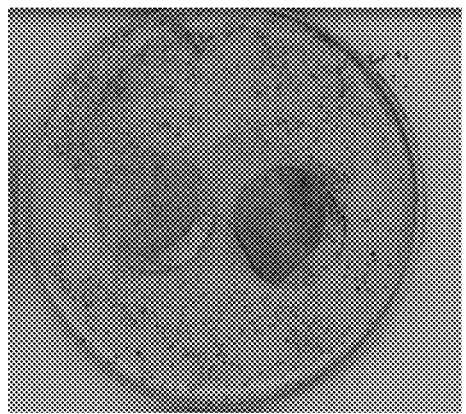
Figure 8A:
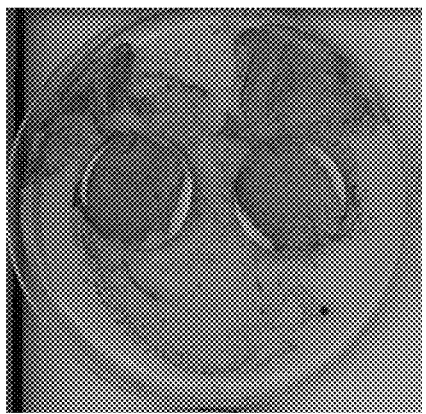
Figure 8A:
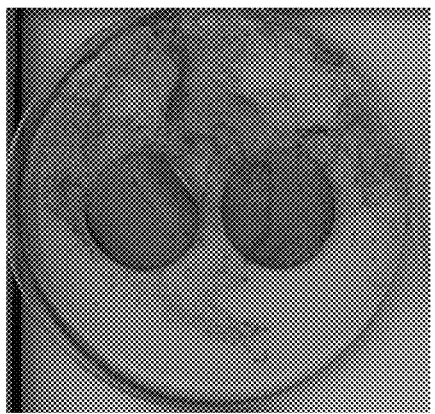
Figure 8A:
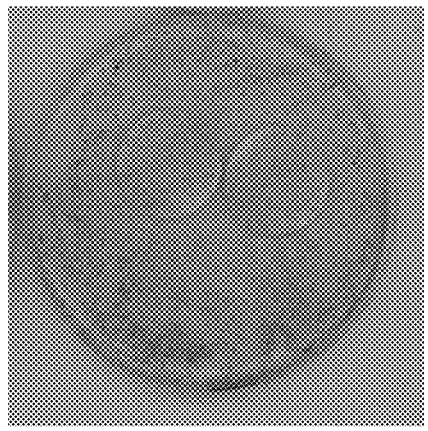
Figure 8A:
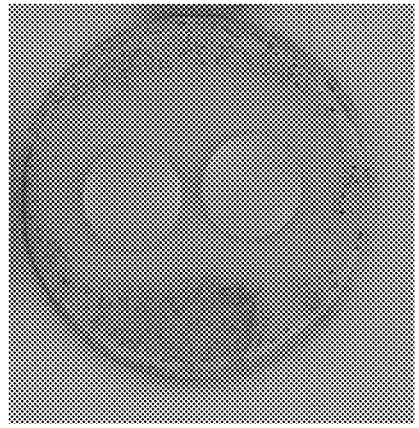
Figure 8B:
Figure 8B:
Figure 8B:
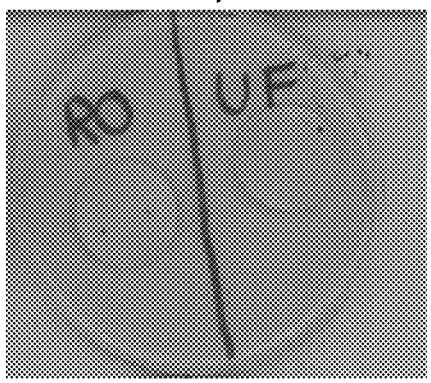
Figure 8B:
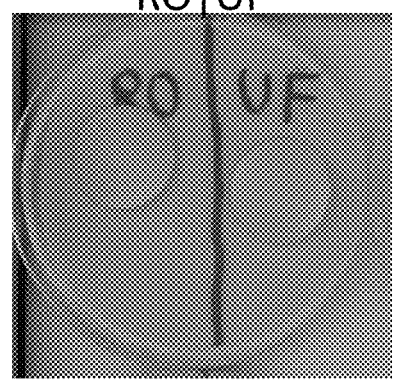
Figure 8B:
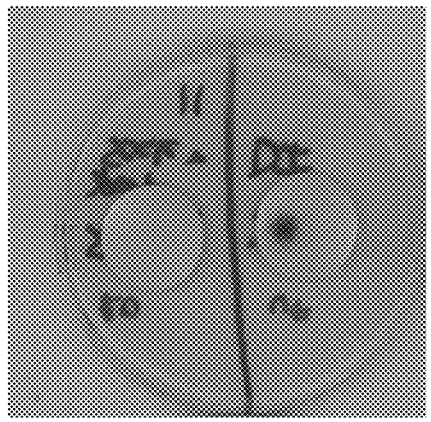
Figure 8B:
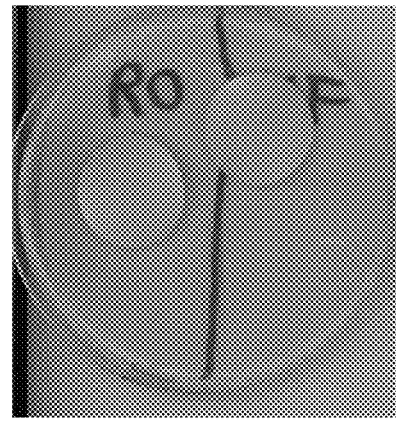

The results of the plating are shown in FIGS. 8A-8B. *Bacillus* sp. spore field isolates diluted in AC-A 1% did not grow on the UF membranes or the surrounding nutrient agar. This held true for membranes soaked in DI water or AC-A 1% prior to spore exposure. *Bacillus* sp. spore field isolates adhered and grew on RO membrane surfaces more than what was observed for UF PES membrane surfaces. Both RO and UF membrane surfaces soaked in DI water and exposed to *Bacillus* sp. spore field isolates diluted in DI water all showed the most adhesion and growth.

Example 7

Efficacy testing was run on field isolates of *Bacillus* sp. spores. Testing was run at several different temperatures (70° F., 110° F. and 122° F.) for a contact time of 5 min. Using SOP #MS009; Germicidal and Detergent Sanitizing Action of Disinfectants as the test method. The suspension method described above in Example 1 was utilized. A new combination treatment of Acid Cleaner B (AC-B) and O-A was compared to AC-A, AC-B, and O-A individually as well as the combination of AC-A with O-A.

Figure 9:
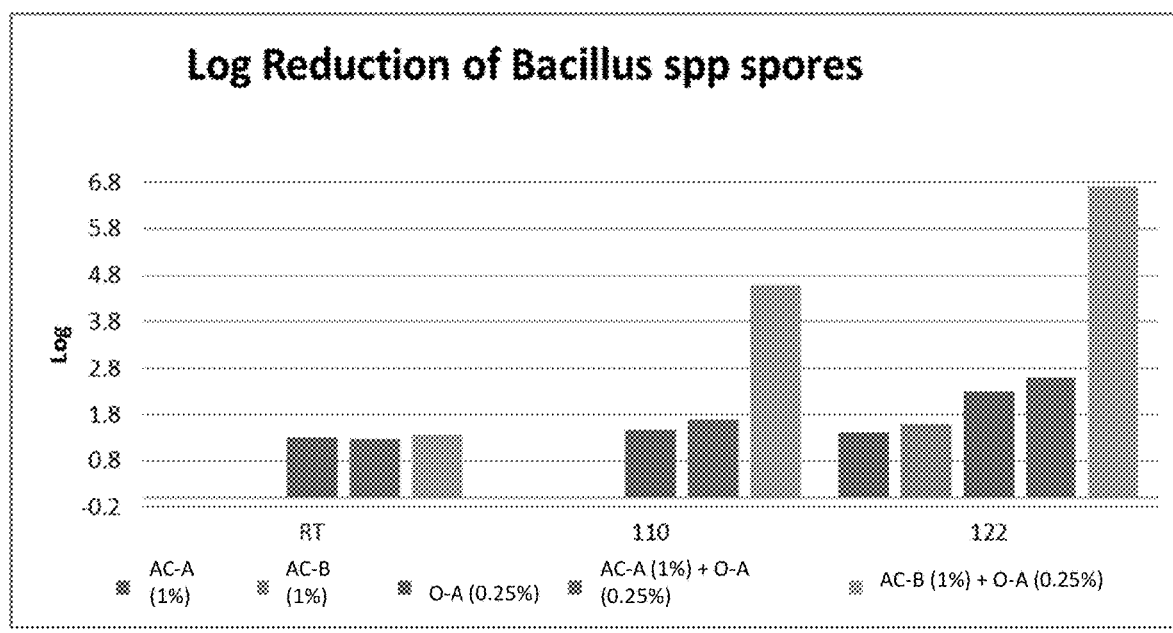
FIG. 9 illustrates a graph comparing the performance of different combinations of antimicrobial compositions for reducing bacterial spores on membranes.

Both combination treatments outperformed the individual solutions at 122° F. and 110° F., as shown in the graph of FIG. 9. AC-B+O-A performed well above everything else. This indicates that the AC-B formula is superior over the AC-A formula when combined with O-A for the reduction of bacterial spores.

Figure 10:
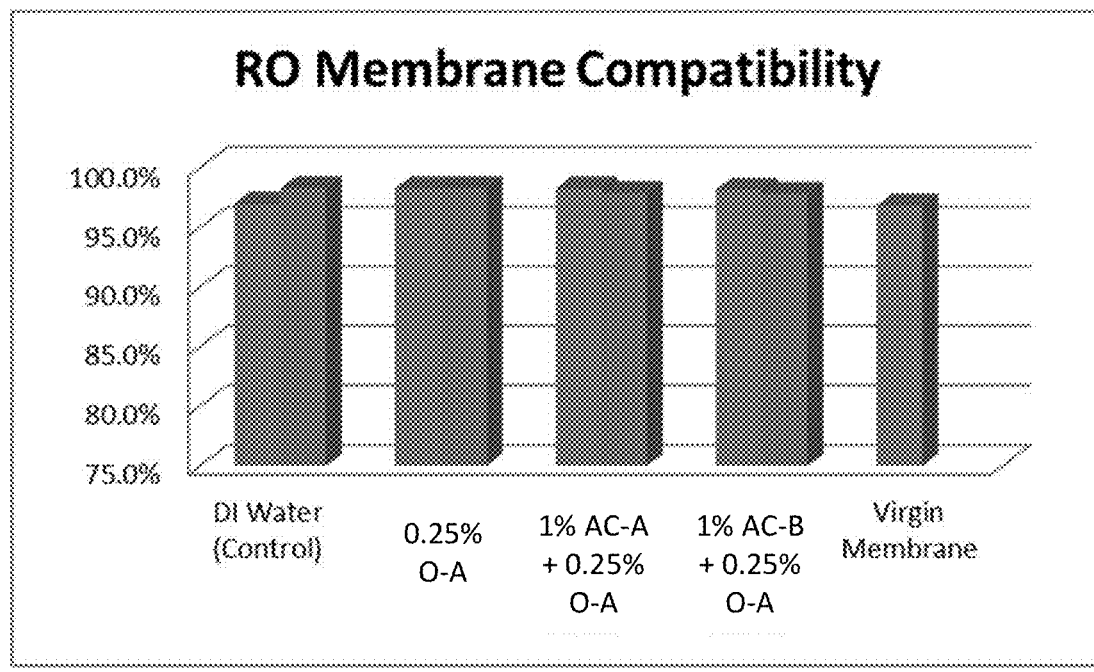
FIG. 10 illustrates a graph comparing RO membrane compatibility after treatment with different combinations of antimicrobial compositions.

FIG. 10 shows a graph demonstrating further RO compatibility testing simulating 1.5 years of chemical exposure using the new experimental formulation. Experimental conditions are as described above in Example 5.

Example 8

The example formulas, including AC-B were tested for performance in removing bacterial spores from membranes. The efficacy of O-A was compared with combinations of O-A with AC-A and O-A with AC-B.

A mixed spore stock of powdered milk spore isolates (*Bacillus*) was diluted in sterile deionized water to approximately $1 \times 10^6$ spores/mL. 1 inch diameter membrane disks were prepared in 1% AC-A solution prior to testing. Each disk was rinsed with sterile DI water to remove the AC-A solution. 24 UF PES membrane disks were immersed in 10/mL of the working spore stock solution per membrane at room temperature for 24 hours. After soaking, the individual membrane disks were rinsed with sterile DI water and stored in sterile 50 mL plastic containers. The membranes were incubated at 110° F. for 5 minutes in a treatment solution. The following treatments were tested: (1) Control, DI water, (2) O-A at 0.25%, (3) AC-A at 1% with O-A at 0.25%, (4) AC-B at 1% with O-A at 0.25%. The membrane disks were then placed in petri dishes containing agar and were incubated at 35° C. for 48 hours.

Figure 11:
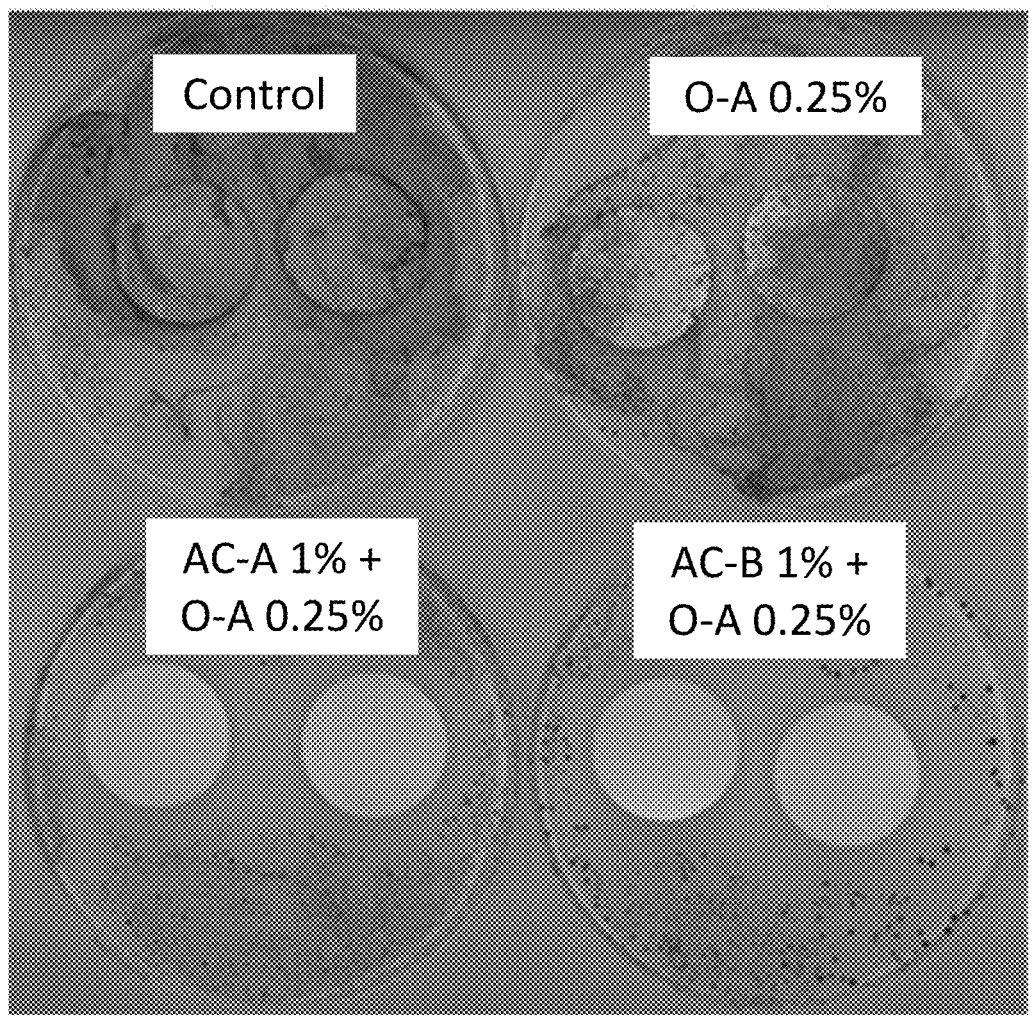
FIG. 11 shows RO and UF membranes treated with different combinations of antimicrobial compositions to eliminate bacterial spores.
Figure 12:
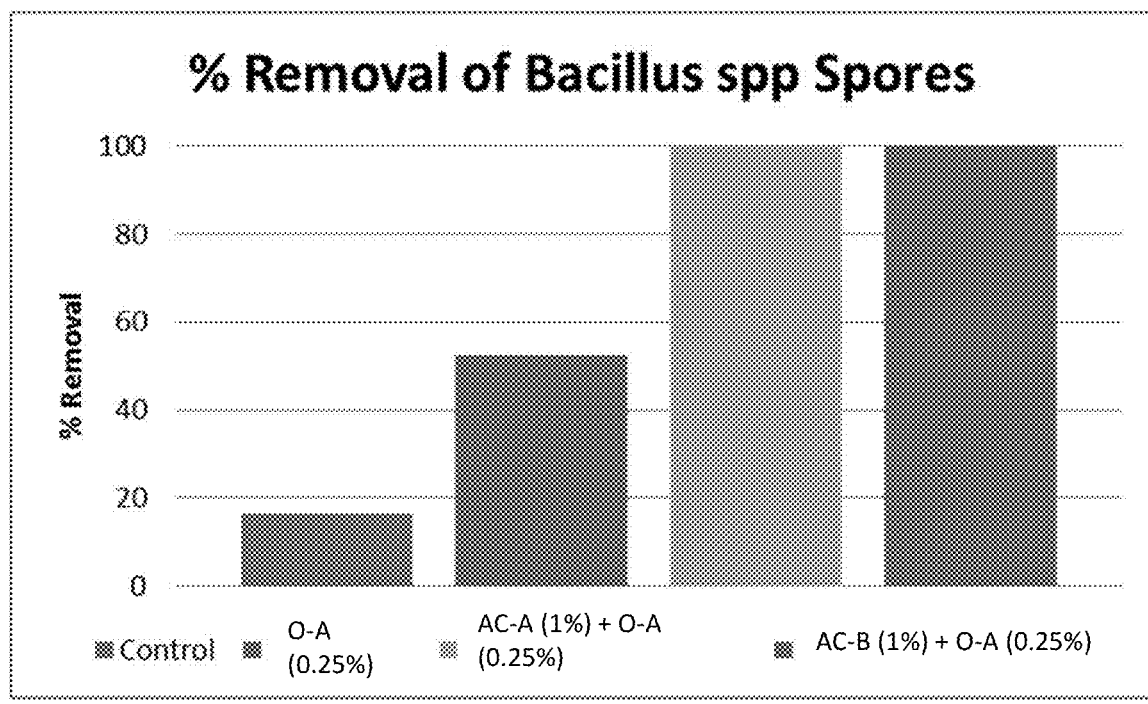
FIG. 12 illustrates a graph comparing the performance of different combinations of antimicrobial compositions for reducing bacterial spores on membranes.

FIG. 11 shows the petri dishes after treatment. FIG. 12 illustrates a graph representing the results. As expected, very little spore removal occurred with the control treatment of water. O-A alone eliminated about half of the spores. Both the combination of AC-A with O-A and AC-B with O-A were more effective for removing bacterial spores than O-A alone. The efficacy of AC-A versus AC-B was about the same. As can be seen in the membranes of FIG. 11, all of the spores were eliminated from the PES membrane disks.

This was followed by examining the efficacy of the example solutions on reducing biofilm produced by *Pseudomona aeruginosa* on a dairy membrane. The CDC Biofilm Reactor was used with an incubation time of 48 hours. Once bacteria are introduced into the Reactor, it takes 24 hours in static state and 24 hours in flow state to grow biofilm on the membranes. Each membrane was subjected to treatment for 5 minutes at 122° F. with one of the following: (1) AC-A, (2) O-A, (3) AC-B, (4) AC-A with O-A, and (5) AC-B with O-A.

Figure 13:
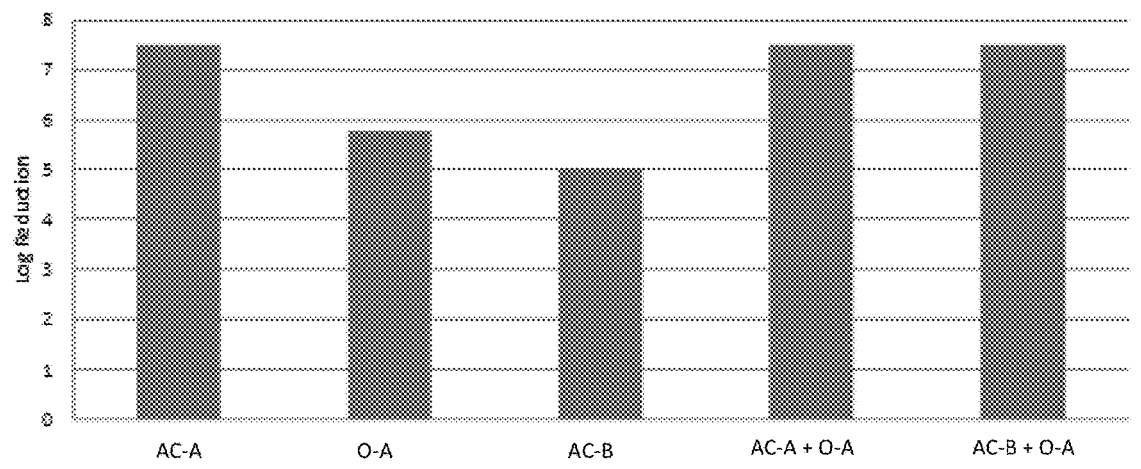
FIG. 13 illustrates a graph comparing the performance of different combinations of antimicrobial compositions for reducing biofilm on membranes.

The results are provided in Table 10 and are illustrated in the graph of FIG. 13. The results showed that AC-B alone was the least effective for reducing biofilm from a dairy membrane but still resulted in a 5.04 log reduction. AC-A performed the best as an individual treatment, with a log reduction of 7.52. The combinations of AC-A with O-A and AC-B with O-A had the same efficacy against the biofilms as AC-A alone, with a log reduction of 7.52.

TABLE 10

Results of Biofilm Reduction (*Pseudomonas aeruginosa*)

| Test Substance | Exposure Time | Rep | Plate Count | Plate Dilution | CFU/mL | CFU/carrier* | Log10 Growth | Avg. Log10 Growth | Log10 Reduction | Standard Deviation |
|---|---|---|---|---|---|---|---|---|---|---|
| AC-A | 5 minutes | 1 | 0.1 | 10 | 1.00E+00 | 4.00E+01 | 1.60 | 1.60 | 7.52 | 0.00 |
|  |  | 2 | 0.1 | 10 | 1.00E+00 | 4.00E+01 | 1.60 |  |  |  |
|  |  | 3 | 0.1 | 10 | 1.00E+00 | 4.00E+01 | 1.60 |  |  |  |
| O-A | 5 minutes | 1 | 2 | 10 | 2.00E+01 | 8.00E+02 | 2.90 | 3.36 | 5.76 | 0.45 |
|  |  | 2 | 6 | 10 | 6.00E+01 | 2.40E+03 | 3.38 |  |  |  |
|  |  | 3 | 16 | 10 | 1.60E+02 | 6.40E+03 | 3.81 |  |  |  |
| AC-B | 5 minutes | 1 | 38 | 10 | 3.80E+02 | 1.52E+04 | 4.18 | 4.08 | 5.04 | 0.11 |
|  |  | 2 | 23 | 10 | 2.30E+02 | 9.20E+03 | 3.96 |  |  |  |
|  |  | 3 | 32 | 10 | 3.20E+02 | 1.28E+04 | 4.11 |  |  |  |
| AC-A + O-A | 5 minutes | 1 | 0.1 | 10 | 1.00E+00 | 4.00E+01 | 1.60 | 1.60 | 7.52 | 0.00 |
|  |  | 2 | 0.1 | 10 | 1.00E+00 | 4.00E+01 | 1.60 |  |  |  |
|  |  | 3 | 0.1 | 10 | 1.00E+00 | 4.00E+01 | 1.60 |  |  |  |
| AC-B + O-A | 5 minutes | 1 | 0.1 | 10 | 1.00E+00 | 4.00E+01 | 1.60 | 1.60 | 7.52 | 0.00 |
|  |  | 2 | 0.1 | 10 | 1.00E+00 | 4.00E+01 | 1.60 |  |  |  |
|  |  | 3 | 0.1 | 10 | 1.00E+00 | 4.00E+01 | 1.60 |  |  |  |
| Untreated Controls |  |  | 26 | 1000000 | 2.60E+07 | 1.04E+09 | 9.02 | 9.13 |  |  |
|  |  |  | 43 | 1000000 | 4.30E+07 | 1.72E+09 | 9.24 |  |  |  |

*0.1 reflects a zero growth results, 0.1 is for calculating purposes

Figure 14:
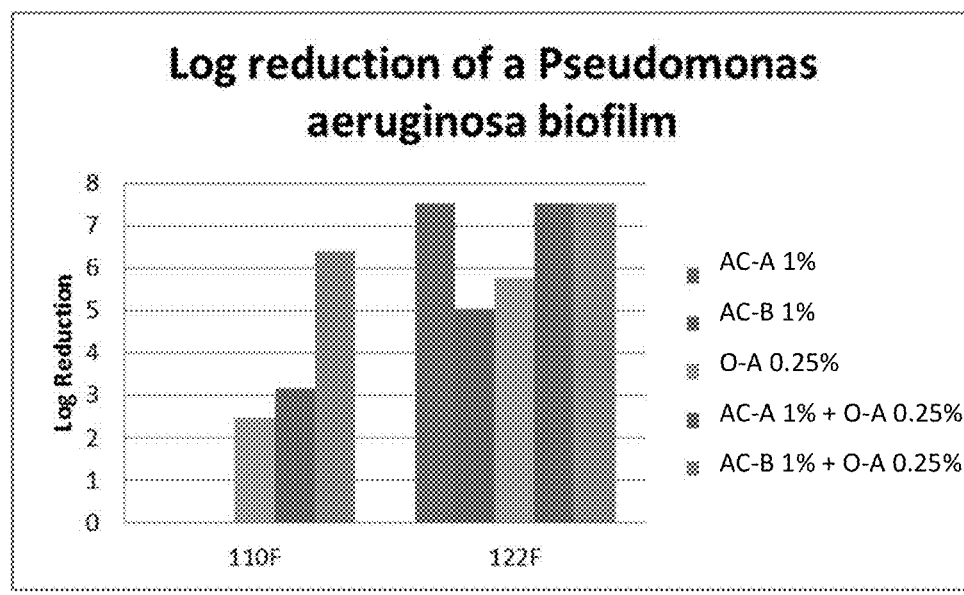
FIG. 14 illustrates a graph comparing the performance of different combinations of antimicrobial compositions at different temperatures for reducing biofilm on membranes.

FIG. 14 illustrates the results of a comparison of the example solutions at 110° F. versus 122° F. These results indicate that treatment at a higher temperature increases the efficacy of the sanitizing treatments.

Example 9

Figure 15:
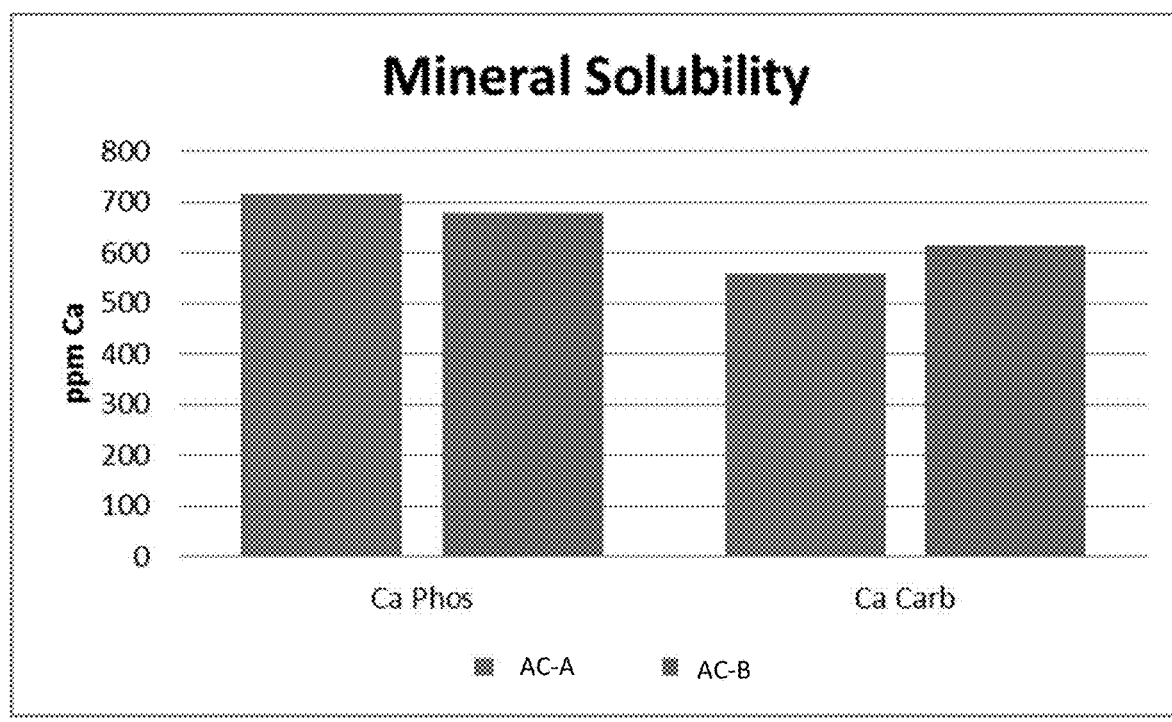
FIG. 15 illustrates a graph comparing the effect of different antimicrobial compositions on mineral solubility.

The example solution combinations of AC-A with O-A and AC-B with O-A were compared for their ability to dissolve calcium. The results are illustrated in FIG. 15.

The description and illustration of one or more embodiments provided in this application are not intended to limit or restrict the scope of the invention as claimed in any way. The embodiments, examples, and details provided in this application are considered sufficient to convey possession and enable others to make and use the best mode of claimed invention. The claimed invention should not be construed as being limited to any embodiment, example, or detail provided in this application. Regardless of whether shown and described in combination or separately, the various features (both structural and methodological) are intended to be selectively included or omitted to produce an embodiment with a particular set of features. Having been provided with the description and illustration of the present application, one skilled in the art may envision variations, modifications, and alternate embodiments falling within the spirit of the broader aspects of the general inventive concept embodied in this application that do not depart from the broader scope of the claimed invention.

While certain embodiments have been described, other embodiments may exist. While the specification includes a detailed description, the scope of the present disclosure is indicated by the following claims. The specific features and acts described above are disclosed as illustrative aspects and embodiments. Various other aspects, embodiments, modifications, and equivalents thereof which, after reading the description herein, may suggest themselves to one of ordinary skill in the art without departing from the spirit of the present disclosure or the scope of the claimed subject matter.

The invention claimed is:

1. A method of cleaning and sanitizing a membrane element within a membrane system, the method comprising:
circulating a cleaning solution through the membrane system for about 2 to about 30 minutes at a temperature of about 70° F. to about 125° F., the cleaning solution consisting essentially of about 0.1 wt. % to about 1 wt. % organic acid, 0 wt. % to about 0.25 wt. % hydrotrope coupler and about 0.01 wt. % to about 0.1 wt. % surfactant, wherein the organic acid in the cleaning solution is a combination of at least two organic acids selected from formic acid, citric acid, and lactic acid;
adding a sanitizing solution to the cleaning solution to produce a boosted antimicrobial solution, the sanitizing solution comprising about 0.02 wt. % to about 0.15 wt. % oxidant, about 0.001 to about 0.03 wt. % acid, about 0.0005 wt % to about 0.01 wt. % stabilizer, and about 0.0001 wt % to about 0.05 wt. % percarboxylic acid; and
circulating the boosted antimicrobial solution through the membrane system for about an additional 1 wt. % to about 20 minutes at a temperature of about 70° F. to about 125° F.;
wherein the method results in at least a 3 log reduction of bacterial spores on the membrane.

2. The method of claim 1, wherein the organic acid in the cleaning solution comprises a combination of citric acid and lactic acid.

3. The method of claim 1, wherein the surfactant comprises an anionic surfactant.

4. The method of claim 1, wherein the surfactant comprises a linear alkyl benzene sulfonate.

5. The method of claim 1, wherein the surfactant comprises dodecyl benzene sulfonic acid (DDBSA).

6. The method of claim 1, wherein the percarboxylic acid comprises peracetic acid.

7. The method of claim 1, wherein the sanitizing solution comprises about 50 ppm to about 250 ppm percarboxylic acid.

8. The method of claim 1, wherein the sanitizing solution comprises hydrogen peroxide, acetic acid, peracetic acid, and hydroxyethylidene diphosphonic acid.

9. The method of claim 1, wherein the method results in at least a 1 log reduction of a biofilm, biofoulant, or slime forming bacteria.

10. The method of claim 1, wherein the method results in at least 3 log reduction of a biofilm, biofoulant, or slime forming bacteria.

11. The method of claim 1, wherein the combination of organic acids, anionic surfactant, and percarboxylic acid results in improved chemical compatibility with the membrane as compared to percarboxylic acid alone, where the improved chemical compatibility is shown by protein rejection of UF membranes or salt rejection of RO membranes.

12. The method of claim 1, wherein the membrane system is a membrane filtration system in a dairy plant, brewery, winery, water plant, or food plant.

13. The method of claim 1, wherein the method is a clean-in-place method.

14. The method of claim 1, wherein the membrane is selected from microfiltration (MF) membranes, ultrafiltration (UF) membranes, nanofiltration (NF) membranes, and reverse osmosis (RO) membranes.

15. The method of claim 1, wherein the membrane is made of polymer, ceramic, or stainless steel.

16. The method of claim 1, wherein the membrane is configured as a spiral wound membrane, hollow fiber membrane, tubular membrane, or a plate and frame flat sheet membrane.

* * * * *

UNITED STATES PATENT AND TRADEMARK OFFICE
CERTIFICATE OF CORRECTION

PATENT NO. : 11,241,658 B2
APPLICATION NO. : 16/274487
DATED : February 8, 2022
INVENTOR(S) : Paul Frazer Schacht et al.

Page 1 of 1

It is certified that error appears in the above-identified patent and that said Letters Patent is hereby corrected as shown below:

In the Claims

Column 20, Line 34: "% oxidant, about 0.001 to about 0.03 wt. % acid, about" should read
--% oxidant, about 0.001 wt. % to about 0.03 wt. % acid, about--

Column 20, Line 35: "0.0005 wt % to about 0.01 wt. % stabilizer, and about" should read
--0.0005 wt. % to about 0.01 wt. % stabilizer, and about--

Column 20, Line 36: "0.0001 wt % to about 0.05 wt. % percarboxylic acid" should read
--0.0001 wt. % to about 0.05 wt. % percarboxylic acid--

Column 20, Line 39: "membrane system for about an additional 1 wt. % to" should read
--membrane system for about an additional 1 to--

Signed and Sealed this
Eighth Day of August, 2023

Katherine Kelly Vidal
*Director of the United States Patent and Trademark Office*